US008609651B2

(12) United States Patent
Jamieson et al.

(10) Patent No.: US 8,609,651 B2
(45) Date of Patent: Dec. 17, 2013

(54) PHARMACEUTICAL COMPOSITIONS OF BENZODIAZEPINES AND METHOD OF USE THEREOF

(75) Inventors: Gene Jamieson, Boulder Creek, CA (US); Michael Des Jardin, Sunnyvale, CA (US); Clark Allphin, Los Altos, CA (US); Sigridur Olafsdottir, Reykjavik (IS)

(73) Assignee: Jazz Pharmaceuticals, Inc., Palo Alto, CA (US)

( * ) Notice: Subject to any disclaimer, the term of this patent is extended or adjusted under 35 U.S.C. 154(b) by 1205 days.

(21) Appl. No.: 11/897,028

(22) Filed: Aug. 27, 2007

(65) Prior Publication Data
US 2008/0070904 A1 Mar. 20, 2008

Related U.S. Application Data
(60) Provisional application No. 60/840,568, filed on Aug. 28, 2006.

(51) Int. Cl.
*A01N 43/62* (2006.01)
(52) U.S. Cl.
USPC .......................................... 514/221; 514/220
(58) Field of Classification Search
None
See application file for complete search history.

(56) References Cited

U.S. PATENT DOCUMENTS

| | | | |
|---|---|---|---|
| 4,950,664 A | 8/1990 | Goldberg | |
| 5,328,099 A | 7/1994 | Petit et al. | |
| 5,584,417 A | 12/1996 | Graf et al. | |
| 5,693,608 A | 12/1997 | Bechgaard | |
| 5,942,237 A | 8/1999 | Gizurarson et al. | |
| 6,193,985 B1 | 2/2001 | Sonne | |
| 6,446,839 B1 | 9/2002 | Ritsche | |
| 6,478,196 B2 | 11/2002 | Fuchs | |
| 6,488,953 B2 | 12/2002 | Halliday et al. | |
| 6,610,271 B2 | 8/2003 | Wermeling | |
| 6,627,211 B1 | 9/2003 | Choi et al. | |
| 6,699,849 B1 | 3/2004 | Loftsson et al. | |
| 6,705,493 B1 | 3/2004 | Mijers et al. | |
| 6,742,677 B2 | 6/2004 | Petit et al. | |
| 6,855,332 B2 | 2/2005 | Gizurarson et al. | |
| 7,080,759 B2 | 7/2006 | Petit | |
| 7,262,185 B2 * | 8/2007 | Shiraishi et al. | 514/213.01 |
| 2003/0219472 A1 * | 11/2003 | Pauletti et al. | 424/449 |
| 2004/0176359 A1 * | 9/2004 | Wermeling | 514/221 |
| 2005/0163719 A1 | 7/2005 | Dugger | |
| 2006/0153905 A1 | 7/2006 | Carrara | |
| 2008/0076761 A1 | 3/2008 | Jamieson et al. | |

FOREIGN PATENT DOCUMENTS

| | | |
|---|---|---|
| AU | 2007290589 B2 | 7/2012 |
| CN | 1056812 | 12/1991 |
| CN | 200780039946.7 | 7/2012 |
| EP | 0324725 A1 | 7/1989 |
| EP | 0324725 | 3/1993 |
| EP | 1587514 A1 | 10/2005 |
| EP | 1652518 | 5/2006 |
| EP | 1652518 A1 | 5/2006 |
| EP | 1587514 | 6/2006 |
| FR | 2656303 | 6/1991 |
| FR | 2656303 A1 | 6/1991 |
| WO | WO 91/16929 | 11/1991 |
| WO | WO-9116929 A1 | 11/1991 |
| WO | WO-9529678 A1 | 11/1995 |
| WO | WO 01/06987 | 2/2001 |
| WO | WO-0106987 A2 | 2/2001 |
| WO | WO 02/11768 | 2/2002 |
| WO | WO-0211768 A1 | 2/2002 |
| WO | WO 03/070273 | 8/2003 |
| WO | WO 03/070280 | 8/2003 |
| WO | WO-03070273 A1 | 8/2003 |
| WO | WO-03070280 A2 | 8/2003 |
| WO | WO 2004/004783 | 1/2004 |
| WO | WO-2004004783 A1 | 1/2004 |
| WO | WO 2004/110403 | 12/2004 |
| WO | WO-2004110403 A1 | 12/2004 |
| WO | WO-2005039531 A1 | 5/2005 |
| WO | WO 2006/075123 | 7/2006 |
| WO | WO-2006075123 A1 | 7/2006 |
| WO | WO 2006/122217 | 11/2006 |
| WO | WO-2006122217 A2 | 11/2006 |
| WO | WO-2008027357 A2 | 3/2008 |
| WO | WO-2008027357 A3 | 3/2008 |
| WO | WO-2008027395 A2 | 3/2008 |
| WO | WO-2008027395 A3 | 3/2008 |

OTHER PUBLICATIONS

"European Application Serial No. 07811570.6 , Office Action Response Filed Nov. 4, 2010", 15 pgs
"European Application Serial No. 07837400.6, Office Action Response Filed Nov. 2, 2010", 13 pgs.
"International Application Serial No. PCT/US2007/018877, International Preliminary Report on Patentability mailed Mar. 3, 2009", 11 pgs.
"International Application Serial No. PCT/US2007/018942, International Preliminary Report on Patentability mailed Mar. 3, 2009", 13 pgs.
"Israeli Application Serial No. 197275, Office Action mailed Mar. 23, 2010", 9 pgs. .

(Continued)

*Primary Examiner* — David J Blanchard
*Assistant Examiner* — Daniel F Coughlin
(74) *Attorney, Agent, or Firm* — Schwegman Lundberg & Woessner, P.A.

(57) ABSTRACT

The present invention includes benzodiazepine compositions formulated for intranasal administration, comprising a binary solvent system comprising a first solvent in which the benzodiazepine is soluble, the first solvent capable of penetrating nasal mucosal tissue, and a second solvent in which the benzodiazepine in less soluble. The compositions of the present invention may be used to treat a variety of disorders including, but not limited to, panic attacks, muscle spasms, anxiety, and seizures. In one aspect, the present invention relates to a fast-acting, clonazepam composition for transnasal administration that can be used for the treatment of seizure clusters.

32 Claims, 4 Drawing Sheets

(56) References Cited

OTHER PUBLICATIONS

"Israeli Application Serial No. 197275, Office Action Response filed Sep. 28, 2010 to Office Action mailed Mar. 23, 2010", 2 pgs.
"New Zealand Application Serial No. 575744, Examiner Report mailed Aug. 6, 2010", 3 pgs.
Dreifuss, "A Comparison of Rectal Diazepam Gel and Placebo for Acute Repetitive Seizures" N. Engl. J. Med 338(26) 1869-1875 (1998).
Mura, "Evaluation of Transcutol as a Clonazepam Transdermal Permeation Enhancer", Eur. J. Pharma. Sci 9, 365-372, (2000).
Hou, "Enhanced Permeation of Diazepam through Artificial Membranes from Supersaturated Solutions", J. Pharma. Sciences 95(4), 896-905 (2001).
Schols-Hendriks, J. Clin. Pharmac 39, 449-451 (1995).
"New Zealand Application Serial No. 575744, Response filed Feb. 3, 2011 to First Examiner Report mailed Aug. 6, 2010", 29 pgs.
"Peruvian Application Serial No. 1144-2007, Office Action mailed Jan. 11, 2011", 4 pgs.
"Peruvian Application Serial No. 1144-2007, Response filed Aug. 17, 2009 to Office Action mailed Jul. 9, 2009", 1 pg.
Crankshaw et al., "The Effect of Solvents on the Potency of Chlordiazepoxide, Diazepam, Medazepam and Nitrazepam", J Pharm. and Pharmacology, 23:5, 1971, 313-321.
Puglia et al., "Evaluation of in Vitro Percutaneous Absorptioin of Lorazepam and Clonazepam from Hydro-Alcoholic Gel Formulations", Int. J. Pharmaceutics, 228:1-2, 2001 79-87.
"U.S. Appl. No. 11/897,002, Restriction Requirement mailed May 3, 2011", 7 pgs.
"Chinese Application Serial No. 200780039946.7, Office Action mailed Feb. 11, 2011", 6 pgs.
"Israel Application Serial No. 197275,Office Action mailed Apr. 13, 2011", 2.
"Peruvian Application Serial No. 1144-2007, Office Action Response Filed Mar. 28, 2011", 11 pages.
"U.S. Appl. No. 11/897,002, Preliminary Amendment mailed Mar. 4, 2009", 18 pgs.
"European Application Serial No. 07811570.6 , Office Action mailed May 3, 2010", 12 Pgs.
"European Application Serial No. 07837400.6, Office Action mailed May 3, 2010", 9 Pgs.
"Peruvian Application No. 1144-2007, Office Action Mailed on Jul. 9, 2009", 1 pg.
Bechgaard, E., et al., "Solubilization of various benzodiazepines for intranasal administration, a pilot study", Pharm Dev Technol., 2(3), (Aug. 1997), 293-6.
Crankshaw, D. P, et al., "The effect of solvents on the potency of chlordiazepoxide, diazepam, medazepam and nitrazepam", J Pharm Pharmacol., 23(5), (May 1971), 313-21.
Dreifuss, "A Comparison of Rectal Diazepam Gel and Placebo for Acute Repetitive Seizures", N. Engl. J. Med 338(26), (1998), 1869-1875.
Hou, H., et al., "Enhanced permeation of diazepam through artificial membranes from supersaturated solutions.", J Pharm Sci., 95(4), (Apr. 2006), 896-905.
Mura, P., et al., "Evaluation of transcutol as a clonazepam transdermal permeation enhancer from hydrophilic gel formulations", Eur J Pharm Sci., 9(4), (Feb. 2000), 365-72.
Puglia, C., et al., "Evaluation of in vitro percutaneous absorption of lorazepam and clonazepam from hydro-alcoholic gel formulations", Int J Pharm., 228(1-2), (Oct. 9, 2001), 79-87.
Schols-Hendriks, "Absorption of clonazepam after intranasal and buccal administration", J. Clin. Pharmac 39, (1995), 449-451.
Vyas, T. K, et al., "Intranasal mucoadhesive microemulsions of clonazepam: preliminary studies on brain targeting", J Pharm Sci., 95(3), (Mar. 2006), 570-80.
"U.S. Appl. No. 11/897,002 , Response filed Oct. 11, 2011 to Non Final Office Action mailed Jul. 19, 2011", 22 pgs.
"U.S. Appl. No. 11/897,002, Non Final Office Action mailed Jul. 19, 2011", 35 pgs.
"U.S. Appl. No. 11/897,002, Response filed Jun. 3, 2011 to Restriction Requirement mailed May 3, 2011", 14 pgs.
"Australian Application No. 2007290589, First Examiner Report mailed Sep. 21, 2011", 2 pgs.
"Chilean Application Serial No. 2457-2007, Office Action mailed Oct. 11, 2011", 2 pgs.
"Chinese Application Serial No. 200780039946.7, Response filed Jun. 24, 2011 to Non Final Office Action mailed Feb. 11, 2011", 12.
"Israeli Application Serial No. 197275, Response filed Aug. 11, 2011 to Non Final Office Action dated Apr. 13, 2011", 5.
"New Zealand Application Serial No. 575744, Response filed Sep. 29, 2011 to Office Action mailed Feb. 23, 2011", 95 pgs.
"New Zealand Application Serial No. 595388, Office Action mailed Oct. 7, 2011", 1 pg.
"Peruvian Application Serial No. 1144-2007, Final Office Action mailed Aug. 3, 2011", 9 pgs.
"U.S. Appl. No. 11/897,002 , Response filed Mar. 7, 2012 to Final Office Action mailed Jan. 20, 2012", 26 pgs.
"U.S. Appl. No. 11/897,002, Advisory Action mailed Mar. 23, 2012", 3 pgs.
"U.S. Appl. No. 11/897,002, Response filed Apr. 20, 2012 to Final Office Action mailed Jan. 20, 2012", 27 pgs.
"Australian Application Serial No. 2007290589, Response filed Mar. 5, 2012 to Non Final Office Action mailed Sep. 21, 2011", 17 pgs.
"U.S. Appl. No. 11/897,002, Final Office Action mailed Jan. 20, 2012", 40 pgs.
"Chilean Application Serial No. 2457-2007, Office Action Response filed Nov. 8, 2011 to Office Action mailed Oct. 11, 2011", 6 pgs.
"New Zealand Application Serial No. 595388, Response filed Oct. 25, 2011 to Office Action mailed Oct. 7, 2011", 2 pgs.
"U.S. Appl. No. 11/897,002, Final Office Action mailed Feb. 8, 2013", 28 pgs.
"U.S. Appl. No. 11/897,002, Response filed Feb. 14, 2013 to Final Office Action mailed Feb. 8, 2013", 9 pgs.
"Japanese Application Serial No. 2009-526675, Response filed Jan. 29, 2013 to Office Action mailed Oct. 1, 2012", with English Claims, 19 pgs.
"Taiwanese Application Serial No. 96130010, Response filed Jan. 28, 2013 to Office Action mailed Aug. 21, 2012", with English translation of claims, 17 pgs.
Iyakuhin Tenkabutsu Jiten, Yakuji Nippo Limited, First Edition, (1994), p. 63.
"U.S. Appl. No. 11/897,002 , Response filed Dec. 17, 2012 to Non Final Office Action mailed Jun. 25, 2012", 18 pgs.
"Canadian Application Serial No. 2,662,197, Voluntary Amendment filed Nov. 8, 2012", 5 pgs.
"Chilean Application Serial No. 2457-2007, Response filed Jul. 17, 2012 to Office Action mailed Jun. 12, 2012", 9 pgs.
"Israeli Application Serial No. 191257, Office Action mailed Oct. 11, 2012", In English, 2 pgs.
"Japanese Application Serial No. 2009-526675, Office Action mailed Oct. 1, 2012", With English Translation, 12 pgs.
"Japanese Application Serial No. 2009-526683, Office Action mailed Nov. 22, 2012", With English Translation, 6 pgs.
"Taiwanese Application Serial No. 96130010, Office Action mailed Jul. 24, 2012", With English Translation, 20 pgs.
Mjiyamae, Yoshikazu, "Shokei (social fear) ni taisuru Yakubutsu ryouhou to Koudou ryouhou no Heiyou", Japan Koudou ryouhou gakkai taikai happyou ronbunnshu, 24(Suppl.), (Nov. 1998), 158-159.
Mura, P, et al., "Evaluation of transcutol as a a clonazepam transdermal permeation enhancer from hydrophilic gel formulations", European Journal of Pharmaceutical Sciences, Elsevier, Amsterdam, NL, vol. 9, No. 4, (Feb. 2000), 365-372.
Toru, Michio, "Tokushu Shinkeishou ken shougai no subete II. Chryo 1. Shinkeishou ken shougai no yakubutsu ryouhou no gensoku", Rinsho seishin igaku (Japanese Journal of Clinical Psychiatry), 35(6), (Jun. 2006), 679-693.

* cited by examiner

PHARMACEUTICAL COMPOSITIONS OF BENZODIAZEPINES AND METHOD OF USE THEREOF

TECHNICAL FIELD

This application claims the benefit of priority, under 35 U.S.C. 119(e), to U.S. Provisional Application Ser. No. 60/840,568, filed Aug. 28, 2006 and is incorporated herein by reference.

The present invention relates to formulations, including compositions and dosage forms of benzodiazepines. Described herein are compositions that are useful and efficacious for transmucosal delivery, including intranasal delivery, as well as methods of use and methods of manufacturing for such compositions.

BACKGROUND OF THE INVENTION

Benzodiazepines are a class of antidepressants, anti-panic agents, and muscle relaxants used to ameliorate anxiety, treat panic disorders, induce sleep, relax muscles, and relieve seizures and muscle spasms. Benzodiazepine medications produce these effects by depressing the central nervous system. Clonazepam, alprazolam, chlordiazepoxide, diazepam, lorazepam, oxazepam, estazolam, midazolam, and triazolam are examples of benzodiazepine medications.

Clonazepam is marketed by Hoffman-La Roche under the trade names KLONOPIN® (Hoffmann-La Roche Inc., New Jersey) in the United States and RIVOTRIL® (Hoffmann-La Roche Inc., New Jersey) in Canada, South America, and Europe. The pharmacological profile of clonazepam resembles that of other anxiolytic/sedative benzodiazepine medications, and its anticonvulsive characteristics are like those of other diazepines. Clonazepam can suppress the spike-wave discharge accompanying absence seizures (i.e., petit mal seizures) and reduce amplitude, frequency, duration, and discharge spreading in small-scale motor seizures.

Lorazepam was first introduced in the late 1970's by Wyeth Pharmaceuticals under the trade name Ativan®. It is now manufactured by Wyeth Laboratories, Pennsylvania and distributed by Biovail Pharmaceuticals, New Jersey and is indicated for the management of anxiety disorders or for the short term relief of the symptoms of anxiety or anxiety associated with depressive symptoms. Injectable lorazepam is useful as an initial anticonvulsant medication for the control of status epilepticus.

Diazepam was first marketed as Valium® by Hoffman-LaRoche in the 1960's. Valium is now distributed by Roche Pharmaceuticals, New Jersey. Valium is indicated for the management of anxiety disorder and relief of symptoms of anxiety, for symptomatic relief of acute alcohol withdrawal, adjunctively for relief of skeletal muscle spasm, and adjunctively in convulsive disorders.

Clonazepam is well absorbed orally; maximum blood concentrations typically occur in one to two hours. It is metabolized by the liver and reduced to inactive metabolites that are excreted primarily in the urine. The amount excreted unchanged in the urine is less than 0.5% of a dose. In addition, 9% to 27% of a dose of clonazepam is excreted in the feces. Clonazepam exhibits a half-life that varies from about 18 hours to 50 hours.

Lorazepam is well absorbed orally; maximum blood concentrations typically occur in one to four hours. It is metabolized by the liver and reduced to inactive metabolites that are excreted primarily in the urine. Lorazepam exhibits a half-life that varies from about 8 hours to 24 hours.

Diazepam is well absorbed orally; maximum blood concentrations typically occur in one to two hours. It is metabolized by the liver and reduced to inactive metabolites that are excreted primarily in the urine. Diazepam exhibits a half-life of about 100 hours.

Clonazepam exhibits strong anxiolytic properties and euphoric side effects; therefore, it is considered a "highly potent" benzodiazepine. Specifically, 0.25 mg of clonazepam is roughly equal to 1.0 mg of lorazepam and 5.0 mg of diazepam. Clonazepam's sedative effects are relatively weak in comparison with its strong anticonvulsant and anxiolytic effects. The sedative effects of clonazepam are also weaker than that of other benzodiazepines. Clonazepam appears, to act by simulating the central nervous system actions of GABA, like other benzodiazepines.

Clonazepam is commonly prescribed to treat epilepsy, anxiety disorders, panic attacks, Restless Legs Syndrome (RLS), chronic fatigue syndrome, REM behavior disorder, night terrors, and Tourette's Syndrome. In the treatment of anxiety disorders, low-dose, long-term treatment with clonazepam may be required because of the chronic nature of anxiety. Although benzodiazepines have some potential for abuse, the use of clonazepam in long-term treatment of anxiety disorders is therapeutic and should not be confused with dependence or addiction. Clonazepam also is used for the initial treatment of mania in combination with medications such as lithium, risperidone, or haloperidol. In addition, clonazepam is prescribed to treat the symptoms of Parkinson's disease and schizophrenia and for twitching and pain management. Clonazepam has also been used to reduce and manage Tourette's Syndrome motor tics. In another application, clonazepam has been used to treat Hallucinogen Persisting Perception Disorder (HPPD). Clonazepam is not typically used to treat insomnia because of its relatively weak sedative effects.

For epilepsy patients, clonazepam is indicated for use alone or as an adjunct therapy, and as primary therapy and for refractory patients. Epilepsy is a disorder characterized by transient but recurrent disturbances of brain function that may or may not be associated with impairment or loss of consciousness and abnormal movements or behavior. The primary objective of caring for patients with epilepsy is to restore their functional capacity to its maximal potential. To do this, physicians use a stable regimen of anti-epileptic drugs (AED). Approximately 30% of patients continue to be refractory to AED treatment and often have recurrent seizures that may occur in clusters. Some of these patients may also experience continued seizure activity without regaining consciousness for a prolonged period of time, a condition called status epilepticus. In addition to being life threatening, recurrent seizures and status epilepticus can impact cognition and permanently damage other brain function.

Patients with refractory epilepsy including episodes of seizure clusters and status epilepticus often present at the emergency room where they are treated with IV benzodiazepines, phenyloin and barbiturates. The goal of treatment in the ER is the prompt cessation of seizure activity. Prior to the ER, there are limited treatment options available to these patients and caregivers.

Epileptic seizures are often classified in two types: primary generalized seizures, (seizures that begin with a widespread electrical discharge involving both sides of the brain) and partial seizures (seizures involving one area of the brain). Included among primary generalized seizures are: absence (also known as petit-mal) seizures, myoclonic seizures, atonic and tonic seizures, clonic and clonic-tonic (also known as grand-mal) seizures. Included among partial seizures are simple and complex seizures and secondary generalized seizures.

Clonazepam has been used in the treatment many different epilepsy syndromes and for different types of seizures including Lennox-Gastaut syndrome (petit mal variant), akinetic and myoclonic seizures. Clonazepam is also useful in patients with absence seizures. In Europe, clonazepam, available in IV formulation, is also used in the acute treatment of seizures in the emergency setting. Often patients with history of cluster seizures and status epilepticus will present to the emergency room.

A rectal gel formulation of diazepam is commercially available (Diastat®) for outpatient treatment of increased seizure activity in patients on stable anti-epileptic drug regimen. Diastat® is administered to patients by caregivers and has been effective in aborting seizure activity and thereby reducing ER visits. However, due to the mode of administration, Diastat® has primarily been used in the pediatric population where a parent can rectally administer to their child. Ideally, an outpatient rescue treatment for these epileptic patients would have a quick onset of action terminating the ongoing seizure and prevent recurrence of seizure activity through a long enough duration of effect. The treatment should also be easily administered by caregivers in a culturally acceptable mode of administration that is easily accessible.

The nasal mucosa offers an alternative to oral and parenteral administration; intranasal administration is a practical way to achieve the therapeutic effect of many medications. Advantages of this method are that drugs can be administered readily and simply, and either a localized or a systemic effect can be achieved. Intranasal administration suffers from a significant problem, however: Most drug molecules diffuse slowly and poorly through the nasal mucosa. Therefore, therapeutic levels of the medication cannot be achieved or may not be achieved in time with the progression of the incidence. A further constraint is that the administration volume must be small; usually it is maximally about 150 µL per nostril. If a greater volume of medication is administered, it may drain into the pharynx and be swallowed.

Various intranasal benzodiazepine compositions have been developed. However, some of these compositions exhibit a delayed time to peak plasma concentration, poor absorption, or poor bioavailability. This is unacceptable for treatment or prevention of some disorders, illnesses and symptoms. Some intranasal midazolam formulations, for example, are produced at a pH that causes nasal irritation and burning in many patients.

Accordingly, there is a need for intranasal benzodiazepine compositions with improved properties such as, for example, rapid absorption, time to peak concentration, and bioavailability. Further, a need exists for vehicles in which the solubility of the drug is high but which are non-damaging to the nasal mucosa. There also is a need for intranasal compositions that improve patient compliance.

SUMMARY OF THE INVENTION

In one aspect, the invention is directed to a pharmaceutical composition for transmucosal administration to a mammal, comprising a solvent system comprising a first solvent in which a benzodiazepine is soluble, the first solvent capable of penetrating nasal mucosal tissue, and a second solvent in which the benzodiazepine is less soluble than in the first solvent, wherein the solvent system comprises 10% (weight/weight) or less of an aqueous buffer solution with the caveat that the solvent system does not comprise free polyethylene glycol polymers; and a therapeutically effective amount of a benzodiazepine.

In other embodiments, the pharmaceutical the solvent system may be substantially a single phase and substantially homogeneous, may be substantially free of aqueous buffer, the first solvent may be diethylene glycol monoethylether (DEGEE) or tetrahydrofurfuryl alcohol polyethyleneglycol ether (glycofurol), the first solvent may be present at a weight percent of between about 30% to about 70%, the second solvent may be glycerol triacetate or propylene glycol, and the benzodiazepine may be present at a weight percent of between about 0.1% to about 10%.

In further embodiments, the first and second solvents may be present in equal weight percents, the pH of the aqueous buffer solution may be between about pH 4 to about pH 7, the composition may further comprise one or more components selected from the group consisting of a surfactant, anti-oxidant, pharmaceutically acceptable polymer, polyalcohol, lipid, mucosa penetration enhancing agent, colorant, flavoring agent, anesthetic agent, co-solvent, and agent to adjust osmolarity, the composition may be formulated to be sprayable and the composition may be sprayable at temperatures between −15° and 30° C.

In another aspect, the invention is directed to a pharmaceutical composition for transmucosal administration to a mammal, comprising a solvent system comprising a first solvent comprising one or more components selected from the group consisting of diethylene glycol monoethylether and tetrahydrofurfuryl alcohol polyethyleneglycol ether, and a second solvent comprising one or more component selected from the group consisting of glycerol triacetate or propylene glycol, wherein the solvent system comprises 10% (weight/weight) or less of an aqueous buffer solution with the caveat that the solvent system does not comprise free polyethylene glycol polymers; and a therapeutically effective amount of a benzodiazepine wherein the composition is a single phase and homogeneous.

In further embodiments the composition may be used at a unit therapeutic dose of between about 50 µL and 300 µL, or between 25 and 150 µL.

In another embodiment, the pharmaceutical composition of the invention comprises a benzodiazepine for intranasal administration to a mammal comprising an ethyl ether solvent and a therapeutically effective amount of the benzodiazepine, wherein the composition is a single phase and homogeneous.

In yet another aspect, the pharmaceutical composition of the invention comprises a benzodiazepine for transmucosal administration to a mammal, characterized by (i) a $T_{max}$ of a benzodiazepine, after a single intranasal administration, of no more than 2 hours, and (ii) a bioavailability of the benzodiazepine, after a single intranasal administration, of no less than 30% of the bioavailability of an equivalent dose of the benzodiazepine delivered orally.

In still another aspect, the pharmaceutical composition of the invention comprises a benzodiazepine for transmucosal administration to a mammal, characterized by (i) a $C_{max}$ of the benzodiazepine, after a single intranasal administration, of at least about 75% the $C_{max}$ of an equivalent dose of the benzodiazepine delivered orally, and (ii) a bioavailability of the benzodiazepine, after a single intranasal administration, of no less than 30% of the bioavailability of an equivalent dose of the benzodiazepine delivered orally.

In a further aspect, the pharmaceutical composition of the invention comprises a benzodiazepine for intranasal administration to a mammal, characterized by (i) a ratio of the AUC of the benzodiazepine, after a single intranasal administration, ($AUC_{in}$) to the AUC of an equivalent dose of the benzodiazepine delivered orally ($AUC_{oral}$) of at least about $AUC_{in}$:$AUC_{oral}$=1:3.3, wherein the AUC values are determined over the same time period.

In other aspects, the invention is directed to a method for administering an active agent to a mammal in need thereof, the method comprising delivery of a benzodiazepine to the mammal's bloodstream via the nasal mucosa of the mammal in a dosage form comprising the compositions described above, and the invention is directed to a method of treating a mammal suffering seizures, the method comprising delivery of the benzodiazepine to the mammal's bloodstream via the nasal mucosa of the mammal, wherein the benzodiazepine is delivered in a dosage form comprising a composition described above.

In other embodiments, delivery of the active agent occurs at the onset of the symptoms of seizures, and one or more unit doses may be administered.

In yet another aspect, the invention is directed to a method of manufacturing a benzodiazepine composition, the method comprising mixing a solvent system and benzodiazepine to provide a single-phase, homogeneous solution suitable for intranasal administration of the benzodiazepine.

Still another aspect, the invention is directed to a method of administering an active agent to a mammal in need thereof, wherein a composition described above is administered to a mammal suffering from anxiety attacks selected from the group consisting of panic attacks, social phobia; social anxiety and performance anxiety.

These and other embodiments of the present invention will readily occur to those of ordinary skill in the art in view of the disclosure herein.

DETAILED DESCRIPTION OF THE INVENTION

Figure 1:
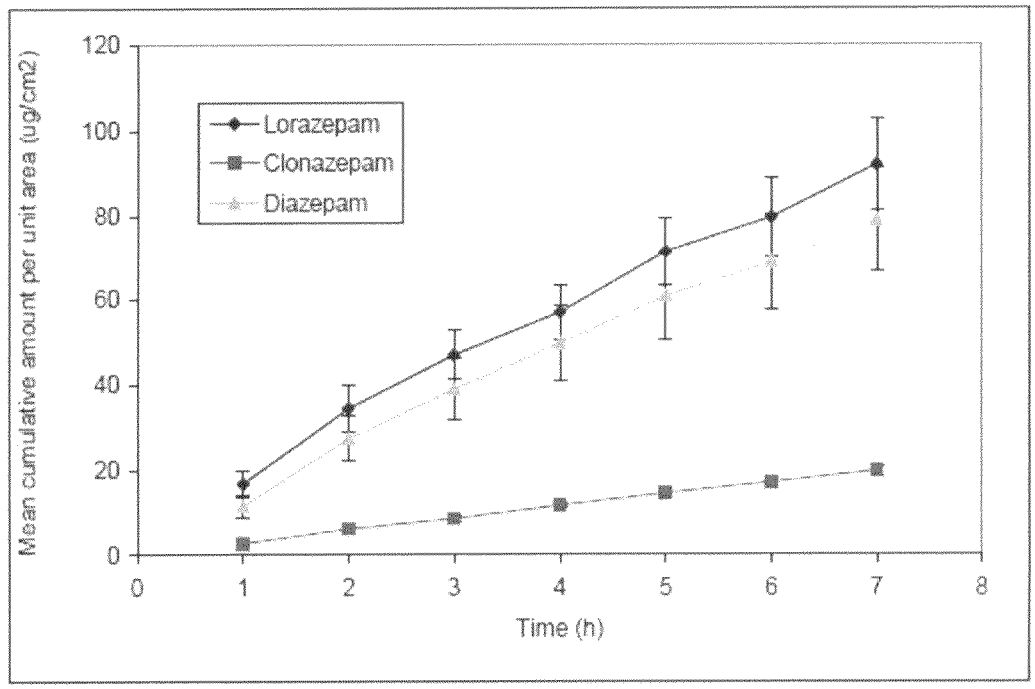
FIG. 1 presents a graphic representation of the mean cumulative amount of diazepam, lorazepam and clonazepam permeated per unit area over a period of 7 hours (h). In the figure, the horizontal axis is Time given in hours (h) and the vertical axis is the mean permeated amount of permeated drug per unit area ($\mu g/cm^2$). The legend for the plot of data is as follows: lorazepam, diamonds; clonazepam, squares; and diazepam, triangles.

All patents, publications, and patent applications cited in this specification are herein incorporated by reference as if each individual patent, publication, or patent application was specifically and individually indicated to be incorporated by reference in its entirety for all purposes.

1.0.0 DEFINITIONS

It is to be understood that the terminology used herein is for the purpose of describing particular embodiments only, and is not intended to be limiting. As used in this specification and the appended claims, the singular forms "a," "an" and "the" include plural referents unless the context clearly dictates otherwise. Thus, for example, reference to "a solvent" includes a combination of two or more such solvents, reference to "a compound" includes one or more compounds, mixtures of compounds, and the like.

Unless defined otherwise, all technical and scientific terms used herein have the same meaning as commonly understood by one of ordinary skill in the art to which the invention pertains. Although other methods and materials similar, or equivalent, to those described herein can be used in the practice of the present invention, the preferred materials and methods are described herein.

In describing and claiming the present invention, the following terminology will be used in accordance with the definitions set out below.

The term "dosage form" as used herein refers to a pharmaceutical composition comprising an active agent, such as a benzodiazepine, and optionally containing inactive ingredients, e.g., pharmaceutically acceptable excipients such as suspending agents, surfactants, solvents, co-solvents, permeation enhancers, binders, diluents, lubricants, stabilizers, anti-oxidants, osmotic agents, colorants, plasticizers, coatings and the like, that may be used to manufacture and deliver active pharmaceutical agents.

The term "gel" as used herein refers to a semi-solid dosage form that contains a gelling agent in, for example, an aqueous, alcoholic, or hydroalcoholic vehicle and the gelling agent imparts a three-dimensional cross-linked matrix ("gellified") to the vehicle. The term "semi-solid" as used herein refers to a heterogeneous system in which one solid phase is dispersed in a second liquid phase. In preferred embodiments of the present invention, the benzodiazepine (e.g., clonazepam) compositions formulated for intranasal delivery are not gellified.

The pH measurements for formulations and compositions described herein, wherein the formulations or compositions do not comprise a predominantly aqueous environment, are more aptly described as "apparent pH" values as the pH values are not determined in a predominantly aqueous environment. In such cases, the influence of, for example, organic solvents on the pH measurement may result in a shift of pH relative to a true aqueous environment.

The term "mucoadhesive" as used herein refers to adhesion to mucous membranes that are covered by mucus, for example, those in the nasal cavity.

The term "carrier" or "vehicle" as used herein refers to carrier materials (other than the pharmaceutically active ingredient) suitable for administration of a pharmaceutically active ingredient, for example, transmucosal administration via nasal mucosa. A vehicle may comprise, for example, solvents, cosolvents, permeation enhancers, pH buffering agents, antioxidants, additives, or the like, wherein components of the vehicle are nontoxic and do not interact with other components of the total composition in a deleterious manner.

The term "transdermal" delivery, as used herein refers to both transdermal (or "percutaneous") and transmucosal administration, that is, delivery by passage of a drug through a skin or mucosal tissue surface and ultimately into the bloodstream. Transmucosal administration includes, but is not limited to, nasal, oral, rectal, and vaginal administration of a composition for delivery of an active drug (e.g., clonazepam) to the blood stream of the subject to which it is administered.

The phrase "therapeutically effective amount" as used herein refers to a nontoxic but sufficient amount of a drug, agent, or compound to provide a desired therapeutic effect, for example, one or more doses of benzodiazepine that will be effective in treatment of seizures including seizure clusters and status epilepticus or for the treatment of anxiety states including but not limited to panic attacks, social phobia, social anxiety and performance anxiety, acute mania, psychosis, and drug withdrawal, including but not limited to nicotine withdrawal, opiate withdrawal, and alcohol withdrawal.

The phrase "seizure clusters" as used herein refers to closely related groups of seizures in some epilepsy patients. Typically seizure cluster patients experience this increased frequency of seizures in unique patterns. It is not uncommon for some of these patients to experience 3 or more seizures in a 24-48 hour period.

The term "benzodiazepine" as used herein refers to a class of drugs with sedative, hypnotic, anxiolytic, anticonvulsant, amnestic and/or muscle relaxant properties. Typically, benzodiazepines comprise a structure composed of a benzene ring fused to a seven-membered diazepine ring. Most of the important benzodiazepines contain an aryl substituent ring and a 1,4-diazepine ring. Generally, benzodiazepine refers to aryl-1,4-benzodiazepines. The actions of benzodiazepines are usually the result of increased activation of receptors by gamma-aminobutyric acid (GABA). The term benzodiazepine includes benzodiazepines and pharmaceutically acceptable salts thereof.

Benzodiazepines are commonly divided into three groups related to the period of time for which the drug has an evident effect: short-acting benzodiazepines typically act for less than six hours; intermediate-acting benzodiazepines typically act for 6-10 hours; and long-acting benzodiazepines have strong sedative effects that persist. The following list is a partial list of benzodiazepines. The list is arranged in an approximate order of the shortest acting to the longest acting benzodiazepine: alprazolam; bromazepam; chlordiazepoxide; clobazam; clonazepam; clorazepate; diazepam; estazolam; flunitrazepam; flurazepam; halazepam; ketazolam; loprazolam; lorazepam; lormetazepam; medazepam; midazolam; nitrazepam; nordazepam; oxazepam; prazepam; quazepam; temazepam; tetrazepam; and triazolam.

Benzodiazepines typically have the following effects, though some may be relatively stronger anxiolytics and others relatively stronger amnesics: anxiolytic (reduce anxiety, e.g., treatment of panic attacks); anticonvulsant (e.g., treatment of seizures); antispasmodic (e.g., muscle relaxant); sedative/hypnotic; antidepressant; and, amnesic (produce anterograde amnesia).

The term "clonazepam" as used herein includes clonazepam and its active pharmaceutically acceptable derivatives and metabolites, as well as pharmaceutically acceptable salts thereof. Clonazepam's pharmacological profile is similar to other anxiolytic/sedative benzodiazepines. Further, the basic anticonvulsive properties of clonazepam are similar to those of other diazepines. Clonazepam is capable of suppressing the spike and wave discharge in absence seizures (petit mal) and decreasing the frequency, amplitude, duration and spread of discharge in minor motor seizures. Clonazepam can be used for the treatment of seizure clusters associated with epilepsy. Chemically, clonazepam is 5-(2-chlorophenyl)-1,3-dihydro-7-nitro-2H-1,4-benzodiazepin-2-one. It is a light yellow crystalline powder. Clonazepam has a molecular weight of 315.72 and the following molecular formula: $C_{15}H_{10}ClN_3O_3$. The structure of clonazepam is as follows:

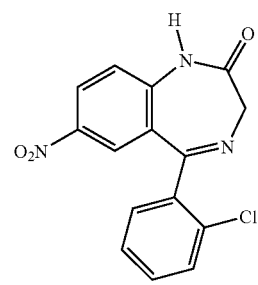 [SMILES: O=C1CN=C(c2ccccc2Cl)c2cc([N+](=O)[O-])ccc2N1]

The term "alkyl solvent" as used herein includes alkyl ethers of 2-5 carbons in length and includes but is not limited to 1,2-dimethoxyoethane, di(ethylene glycol)methyl ether, diethylene glycol monoethyl ether and di(ethyleneglycol)diethyl ether.

The phrase "permeation enhancer" or "penetration enhancer" as used herein refers to an agent that improves the rate of transport of a pharmacologically active agent (e.g., clonazepam) across the mucosal or skin surface. Typically a penetration enhancer increases the permeability of mucosal tissue or skin to a pharmacologically active agent. Penetration enhancers, for example, increase the rate at which the pharmacologically active agent permeates through mucosal tissue and enters the bloodstream. Enhanced permeation effected through the use of penetration enhancers can be observed, for example, by measuring the flux of the pharmacologically active agent across animal or human tissue as described in the Examples herein below. An "effective" amount of a permeation enhancer as used herein means an amount that will provide a desired increase in nasal mucosal tissue permeability to provide, for example, the desired depth of penetration of a selected compound, rate of administration of the compound, and amount of compound delivered.

The term "subject" as used herein refers to any warm-blooded animal, particularly including a member of the class Mammalia such as, without limitation, humans and non-human primates such as chimpanzees and other apes and monkey species; farm animals such as cattle, sheep, pigs, goats and horses; domestic mammals such as dogs and cats; laboratory animals including rabbits and rodents such as mice, rats and guinea pigs, and the like. The term does not denote a particular age or sex.

The term "delivery rate" as used herein refers to the quantity of drug delivered, typically to plasma, per unit time, for example, nanograms of drug released per hour (ng/hr) in vivo.

In the context of plasma blood concentration of active agent, the term "C" as used herein refers to the concentration of drug in the plasma of a subject, generally expressed as mass per unit volume, typically nanograms per milliliter (this concentration may be referred to as "plasma drug concentration" or "plasma concentration" herein which is intended to be inclusive of drug concentration measured in any appropriate body fluid or tissue). The plasma drug concentration at any time following drug administration is typically referred to as $C_{time}$ as in $C_{10h}$ or $C_{20h}$, etc. The term "$C_{max}$" refers to the maximum observed plasma drug concentration following administration of a drug dose, and is typically monitored after administration of a first dose and/or after steady-state delivery of the drug is achieved. The following terms are used herein as follows: "$C_{avg}$" refers to average observed plasma concentration typically at steady state, $C_{avg}$ at steady state is also referred to herein as "$C_{ss}$"; "$C_{min}$" refers to minimum observed plasma concentration typically at steady state.

The term "AUC" or area under the curve as used herein refers to total amount of drug absorbed by the body and is the area under the curve in a plot of concentration of drug in plasma against time and in this case is calculated for humans for 24 hours after administration orally ($AUC_{oral}$), intranasally ($AUC_{in}$) or intraveneously ($AUC_{iv}$).

Figure 5:
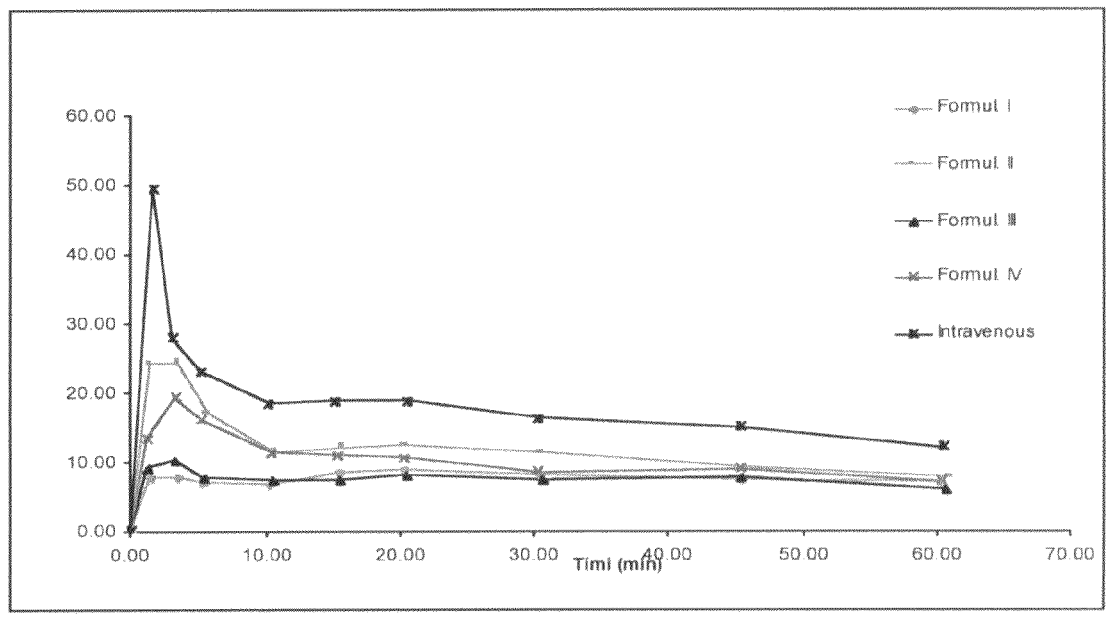
FIG. 5 presents pharmacokinetic data in a rabbit study. In the figure, the vertical axis is concentration of clonazepam (CLZ conc. (ng/mL)), and the horizontal axis is time in minutes (Time (min.)). The legend for the plot of data is as follows: Formulation I, closed circles; Formulation II, closed squares; Formulation III; upright triangles; and Formulation IV, light x's. The top data line with dark x's corresponds to the data for intravenous administration.

The term "$T_{max}$" as used herein refers to the time to maximum plasma concentration and represents the time that elapses between administration of the formulation and a maximum plasma concentration of drug (i.e., a peak in a graph of plasma concentration vs. time, see, for example, FIG. 5). $T_{max}$ values may be determined during an initial time period (for example, related to administration of a single dose of the drug) or may refer to the time period between administration of a dosage form and the observed maximum plasma concentration during steady state.

The term "steady state" as used herein refers to a pattern of plasma concentration versus time following consecutive administration of a constant dose of active agent at predetermined intervals. During "steady state" the plasma concentration peaks and plasma concentration troughs are substantially the same within each dosing interval.

The term "spray" as used herein means a liquid composition expressed from a device under pressure in the form of an aerosol, a fine mist, liquid droplets, a fine stream, or combinations thereof. The precise form of the liquid composition is dependent upon the viscosity and other physical properties, as well as the manner in which a force (manual or other) is applied to a device containing the liquid composition to discharge the liquid composition. Some characteristics of a spray of a liquid composition are described in "Guidance for Industry: Nasal Spray and Inhalation Solution, Suspension, and Spray Drug Products—Chemistry" and further in "Manufacturing, and Controls Documentation" (July 2002), and the Examples, herein below, and include, but are not limited to spray pattern, droplet size, and plume geometry. Typically, the spray is homogeneous, however a heterogeneous spray is acceptable as long as the sprayed volume is effectively adsorbed by the nasal mucosa.

The phrase "with the caveat that the solvent system does not comprise free poly ethylene glycol polymers" as used herein refers to a composition comprising one or more solvents that do not contain polyethylene glycol (PEG) polymers free in the solution of the solvent system, that is the composition does not contain PEG polymers that are not an intrinsic part of a larger chemical entity. Accordingly, free polyethylene glycol polymers (e.g., PEG 200, PEG 300, PEG 400) are not added as separate components to the solvent system. However, a composition that does not comprise free polyethylene glycol polymers may comprise molecules that contain substituent polyethyelene glycol polymers as part of their intrinsic molecular structure (e.g., glycofurol and mono- or di-glycerides that contain PEG polymers as substituent groups (see, for example, published P.C.T. International Application Nos. WO 03/070273, WO 03/070280, and U.S. Pat. Nos. 6,855,332 and 5,942,237)).

The term "free of aqueous buffer" intends a composition that is substantially free of aqueous buffer in that aqueous buffer is not added to the composition.

The term "homogeneous" as used herein refers to a composition that is substantially uniform visually and macroscopically, substantially free of particulates and does not settle or separate over time.

The term "single phase" as used herein refers to a composition that substantially contains one thermodynamic state, and is chemically and physically uniform throughout.

The term "bioavailability" or "F" refers to relative bioavailability and intends the ratio of $AUC_{in}$ to $AUC_{oral}$, in the case of human subjects and intends the ratio of $AUC_{in}$ to $AUC_{iv}$ in the case of rabbits.

The term "unit dose" as used herein refers to the amount of the transmucosal clonazepam required for a therapeutically effective dose. The unit dose may be given in one or more sprays, and for intranasal delivery, may be given in one or both nostrils.

One of ordinary skill in the art appreciates that plasma drug concentrations obtained in individual subjects will vary due to inter-subject variability in many parameters affecting, for example, drug absorption, distribution, metabolism, and excretion. Accordingly, mean values obtained from groups of subjects are typically used for purposes of comparing plasma drug concentration data and for analyzing relationships between in vitro dosage assays and in vivo plasma drug concentrations.

2.0.0 General Overview of the Invention

A seizure cluster can be described as an ictal pattern wherein several seizures occur within a short period, usually days. This period of seizure activity is typically followed by a longer seizure-free interval of weeks to months. According to epidemiologic studies, approximately 50% of epilepsy patients experience seizure clusters. Clustering may be quasi-weekly or quasi-monthly (Tauboll, E., et al., "Temporal distribution of seizures in epilepsy," Epilepsy Res. 8(2), pages 153-165 (1991); Bauer, J., et al., "Course of chronic focal epilepsy resistant to anticonvulsant treatment," Seizure 10(4), pages 239-246 (2001)).

A preferred treatment for seizure clusters would have a rapid action and long duration of action. Further, the treatment should be relatively non-sedating. In addition, the ability to self-administer treatment is often compromised during seizure and oral administration may not be possible. One common treatment in the United States is rectal diazepam gel (Dreifuss, F. E., et al., "A comparison of rectal diazepam gel and placebo for acute repetitive seizures," N. Engl. J. Med. 338(26), pages, 1869-1875 (1998)). Non-oral routes of administration are desirable in that it is often a family member, significant other, or other second party who may recognize the onset of acute repetitive seizures. Oral administration of some benzodiazepines has been used for the treatment of seizure clusters (for example, diazepam given at 5 mg to 10 mg dose, lorazepam given at 1 mg to 2 mg dose, and clonazepam given at 0.5 mg to 2 mg dose. Some benzodiazepine formulations for buccal (e.g., U.S. Pat. No. 6,699,849), transdermal (e.g., Mura, P., et al., "Evaluation of Transcutol® as a clonazepam Transdermal Permeation Enhancer," Eur. J. Pharma. Sci. 9, pages 365-372 (2000)) and mucosal administration (e.g., U.S. Pat. No. 6,488,953) have been described. Further, some benzodiazepine formulations for intranasal administration have been described (see, for example, Hou, H., et al., "Enhanced Permeation of Diazepam through Artificial Membranes from Supersaturated Solutions," J. Pharma. Sciences 95(4), pages 896-905 (2001); Schols-Hendriks, M. W. G., et al., J. Clin. Pharmac. 39, pages 449-451 (1995); U.S. Pat. Nos. 6,193,985, 6,610,271, 6,627,211; U.S. Published Patent Application No. 2004/0176359; Published P.C.T. International Application Nos. WO 2004/110403 and WO 03/070208); however, nasal formulations prior to those of the present invention have had a number of short comings, for example, the formulations comprise benzodiazepines with relatively high sedation properties, formulations have relied on supersaturated solutions that do not store well and may crystallize, serum drug concentrations after administration have been too low to be therapeutically effective, the formulations comprised non-homogeneous systems that present complications for spray delivery, some formulations do not have acceptable tolerability or irritation profiles, or they contain components that lead to degradation of the benzodiazepine.

Some treatments, for example, treatment with oral lorazepam or diazepam, often cause drowsiness and delay the ability of the subject being treated to return to her/his normal activities.

Since the treatment described herein would be relative fast acting and non-sedating, it is also contemplated the intranasal benzodiazepines could be useful to treat other conditions that require fast onset and minimal side effects. These include anxiety states including but not limited to panic attacks, social phobia, social anxiety and performance anxiety; acute mania; psychosis; and drug withdrawal, including but not limited to nicotine withdrawal, opiate withdrawal, and alcohol withdrawal. The treatment may also be useful for patents that are unconscious, semiconscious, and/or unable to swallow.

Some advantages for intranasal delivery of benzodiazepines include the following. Intranasal administration is convenient, simple, easy, non-invasive and virtually pain-free. It neither generates biohazardous waste nor risk of needle-stick accidents. Intranasal formulations can be delivered in precise, metered doses. Further, smaller doses can be administered, for example, serially, to obtain the desired clinical result with fewer side effects (e.g., intestinal) than medication delivered in tablet form. Intranasal administration can provide rapid, efficient absorption and more consistent bioavailability. It also provides flexibility for health care workers, patients, and their caregivers. Unit doses, for example, can reduce abuse potential. Also, intranasal administration avoids first pass metabolism of the benzodiazepine.

Before describing the present invention in detail, it is to be understood that this invention is not limited to particular embodiments described herein, for example, particular benzodiazepines (including, without limitation, clonazepam, diazepam and lorazepam), solvent(s), cosolvent(s), hydrophilic polymer(s), surfactant(s) (including, ionic and non-ionic surfactant(s)), polyalchohol(s), solublizing agent(s), antioxidant(s), penetration enhancer(s), and/or buffering agent(s), and the like, as use of such particulars may be selected in view of the teachings of the present specification by one of ordinary skill in the art. It is also to be understood that the terminology used herein is for the purpose of describing particular embodiments of the invention only, and is not intended to be limiting.

2.1.0 Exemplary Formulations of the Present Invention and Components Thereof 2.1.1 Transmucosal Formulations and Methods of Use In one aspect, the present invention includes a pharmaceutical composition of benzodiazepine (e.g., clonazepam) for transmucosal administration to a mammal. Example 1 presents data obtained in support of the present invention that demonstrated the ability of clonazepam, diazepam and lorazepam as a exemplary benzodiazepines, to penetrate nasal mucosa. The permeation of saturated solutions of the benzodiazepines across nasal sheep mucosa in vitro is described in the example, as are preliminary stability data. FIG. 1 presents a graphic representation of the mean cumulative amount of benzodiazepines permeated per unit area over a period of Example 1. The benzodiazepines were shown to have acceptable stability in the context of use for transmucosal administration, as well as acceptable permeation characteristics through nasal mucosa.

The solubility of clonazepam in a number of neat solvents were determined (Example 2) as part of a determination of suitable solvents for use in benzodiazepine formulations of the present invention for intranasal administration. Good solvents were identified as useful for achieving a target solubility of clonazepam of about 10 to about 20 mg/mL. Further, the solubility of clonazepam in binary solvent mixtures of diethylene glycol mono-ethyl ether, triacetin, glycofurol and propylene glycol was evaluated. The data presented in FIG. 2, for example, demonstrated a linear relationship between the solubility and percent composition of the binary mixtures of triacetin or propylene glycol and glycofurol. The data presented in FIG. 2 demonstrated the usefulness of solvent solutions comprising binary solvent mixtures to solubilize clonazepam for use in formulation of intranasal pharmaceutical compositions.

The solvent systems set forth Example 2 provide examples of formulations of minimum number of solvent components in the system, which helps reduce possible interactions. These solvent combinations also increase the chemical potential and system thermodynamics helping to ensure that the drug (e.g., clonazepam) prefers to leave the solvent system to cross the nasal membrane rather than being swallowed, particularly when mixed with water in the nasal mucosa (i.e., mucocilliary clearance). The solvent systems described in Example 2 also, provide guidance concerning avoiding components that may provide a thermodynamic sink (e.g., polyethylene glycol polymers and cyclodextrins).

The stability of clonazepam in exemplary solvent systems was further examined (Example 3). The data suggested that formulations comprising polyethylene glycol polymers provided the least drug (clonazepam) stability. Further, formulations that contained water without buffer also demonstrated color development, indicative of degradation of the clonazepam. Other solvent systems (for example, including diethylene glycol monoethylether, tetrahydrofurfuryl alcohol polyethyleneglycol ether, glycerol triacetate, propylene glycol, and buffered aqueous solutions) provided good stability for clonazepam.

The data presented in Example 3 also suggested that addition of an anti-oxidant to the formulations of the present invention used for intranasal delivery of benzodiazepines may provide desirable drug protective benefits to such formulations. Further, the data indicated drug protective effects resulting from the inclusion of pH modifiers when an aqueous solvent was used.

In order for benzodiazepine (e.g., clonazepam) formulations to be useful for administration to mucosal membranes, the formulations should have acceptable irritation and tolerance profiles. The preliminary nasal irritation data (Example 4) and the nasal discomfort reports of the human pharmacokinetic study (Example 14) suggested that the benzodiazepine formulations of the present invention were suitable for intranasal delivery. The data shown in FIG. 3 and FIG. 4 demonstrated slight, transient nasal irritation in the test animals. After instillation of compositions, irritation typically lasted less than about two minutes in rats. Irritation was generally greater than saline and similar to irritation from tolerable concentrations of acetic acid. Veterinary evaluation of the data resulted in the conclusion that nasal irritation from these formulations was not significant. Further, the data presented in Example 4 suggests that non-ionic surfactants may possibly be used to reduce nasal irritation in some formulations.

The pharmacokinetics of a large number of clonazepam formulations were evaluated (Example 5, see, for example, Table 12A and 12B). The pharmacokinetic data presented in the example illustrated that clonazepam compositions formulated for intranasal administration are pharmaceutically efficacious to deliver clinically relevant amounts of clonazepam into the bloodstream in a relatively short time period—making such intranasal formulations clinically useful, for example, for the treatment of seizure clusters. The values of the pharmacokinetic parameters vary between the different formulations and one of ordinary skill in the art, following the guidance of the present specification, may select formulations suitable for a variety of treatment purposes, for example, use in adults (generally higher $C_{max}$, and AUC, is desirable), use in children (lower $C_{max}$, and AUC, may be desirable relative to formulations for use in adults), different dosage forms and serial administration (e.g., starting with administration of rapid onset, early $T_{max}$, and following with a second administration of a formulation with slower onset, later $T_{max}$), etc.

Experiments performed in support of the present invention demonstrated that the compositions of the present invention may comprise a solvent matrix of two solvents, for example, a first solvent that provides high solublization of clonazepam (for example, Transcutol® (diethylene glycol monoethylether) and similar monoethylethers, Glycofurol (ethoxylated furanyl alcohol or tetrahydrofurfuryl alcohol polyethyleneglycol ether) and similar ethoxylated tetrahydrofurfuryl alcohols that, after application to nasal mucosa, is absorbed by the nasal mucosa leading to clonazepam super saturation in the nasal cavity, and a second solvent (for example, triacetin and propylene glycol or the like) in which clonazepam has lower solubility relative to the first solvent.

The pharmacokinetics and tolerability of four clonazepam compositions comprising binary solvent systems were evaluated in further detail (Example 5, Table 13). The intranasal PK profiles of the formulations (FIG. 5) demonstrated a rapid absorption of clonazepam such that clinically relevant amounts of clonazepam reach the bloodstream in a short period of time. Lower bioavailability in some formulations can be compensated for with, for example, use of a higher initial dose. An advantage of a higher dose and low short term bioavailability may be passage of the drug that is not absorbed intranasally into the gastro-intestinal tract resulting in the remainder of the drug undergoing classical GI absorption leading to a sustained release profile.

Figure 6:
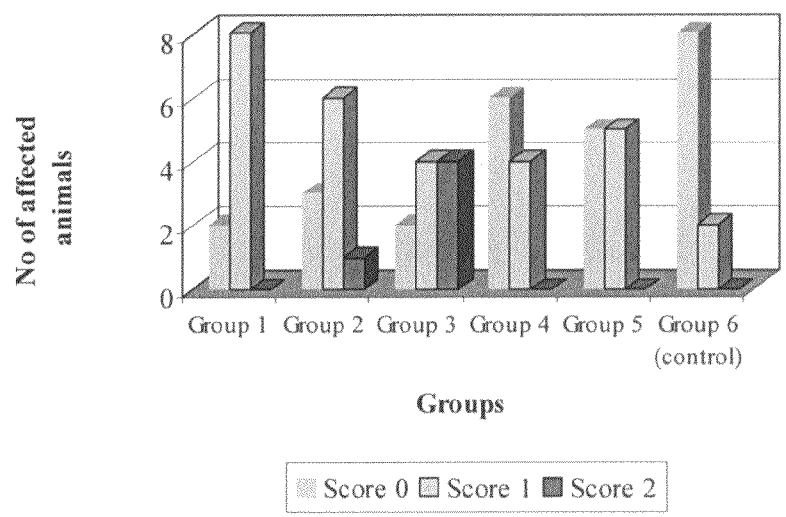
FIG. 6 summarizes the histopathology results for the nasal cavities of test animals to which clonazepam compositions of the present invention were administered. In the figure, the vertical axis is the number of affected animals; and the horizontal axis are the test groups organized by groups of three bar graphs. In each bar graph the order of the vertical bars is as follows: Score 0; Score 1; and Score 2.

Further, experiments performed in support of the present invention evaluated the local tolerance in the upper and lower respiratory tract of four clonazepam compositions of the present invention. Tolerance was assessed using a rabbit model (Example 5). The data presented in FIG. 6 summarizes the histopathology results for the nasal cavities of the animals. The results of necropsy and histopathological examination, including comparison of severity scores, suggested that clonazepam compositions of the present invention have acceptable tolerability for pharmaceutical use for administration to nasal mucosal tissue.

Pharmacokinetic and tolerability were expected to be similarly desirable in humans and were shown to be desirable in 15 human volunteers. Experiments to evaluate pharmacokinetics and tolerability in humans are prophetically described in Example 8, Example 9, and Example 10. Actual experiments and their results are described in Examples 14, 15 and 16.

Figure 7:
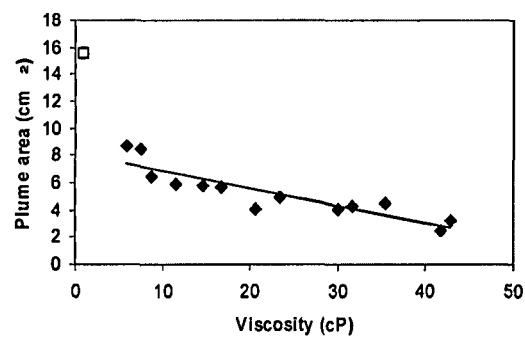
FIG. 7 shows the correlation between plume area at 3 cm and viscosity of non-aqueous solvent matrices. Data for water is shown for comparison (□). Composition of solvent matrices is presented in Table 19. In the figure, the vertical axis is plume area in cm and the horizontal axis is viscosity (cP).
Figure 8:
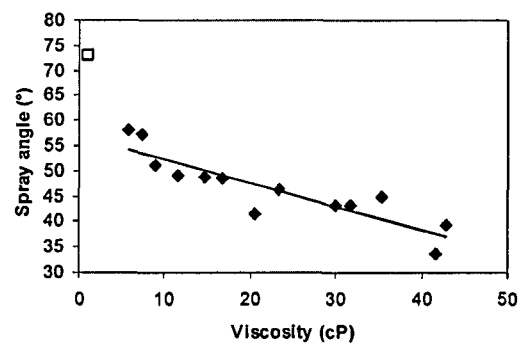
FIG. 8 shows the correlation between spray angle and viscosity of non-aqueous solvent matrices. Data for water is shown for comparison (□). Composition of solvent matrices is presented in Table 19. In the figure, the vertical axis is spray angle (in degrees) and the horizontal axis is viscosity (cP).
Figure 9:
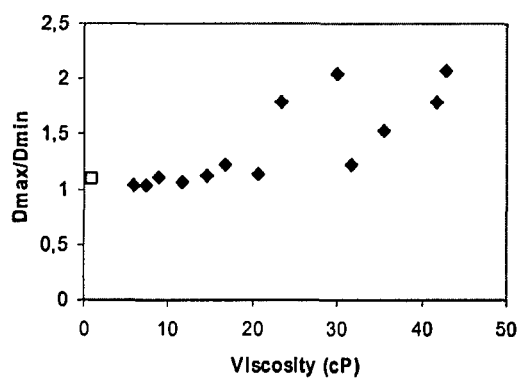
FIG. 9 shows the correlation between plume asymmetry ($D_{max}/D_{min}$) and viscosity of non-aqueous solvent matrices. Data for water is shown for comparison (□). Composition of solvent matrices is presented in Table 19. In the figure, the vertical axis is ($D_{max}/D_{min}$) and the horizontal axis is viscosity (cP).

As one intended use of the formulations of the present invention is for intranasal administration, sprayability (including plume geometry, spray angle, and plume symmetry) and viscosity of exemplary formulations of the present invention were evaluated (Example 6, FIG. 7, FIG. 8, and FIG. 9). The results demonstrated that at 20-25° C. all solvent matrices tested sprayed well from manually activated unit dose devices (e.g., obtained from Pfeiffer, manufactured by Pfeiffer of America, Princeton, N.J.). The results also suggested that viscosity of the formulations of the present invention is a good predictor of sprayability and that the formulations retained their sprayability at temperatures below 40° C., and between −15° C. and 30° C.

In view of the experimental findings discussed herein, the compositions of the present invention of benzodiazepine (e.g., clonazepam, diazepam or lorazepam) for transmucosal administration to a mammal may, for example, comprise a solvent system and a therapeutically effective amount of a benzodiazepine (e.g., clonazepam, diazepam or lorazepam). In one embodiment the solvent system comprises a first solvent in which benzodiazepine (e.g., clonazepam, diazepam or lorazepam) is soluble, the first solvent capable of penetrating nasal mucosal tissue, and a second solvent in which benzodiazepine (e.g., clonazepam, diazepam or lorazepam) is less soluble than in the first solvent. The solvent system may comprise about 40% or less aqueous solvent, about 30% or less, preferably about 20% or less, more preferably about 10%, or less, about 8% or less, about 5% or less, or about 2% or less. The aqueous solvent is preferably a buffered aqueous solution, for example, with a pH of the aqueous buffer solution between about pH 4 to about pH 7, more preferably between about pH 4 to pH 5.5. In preferred embodiments, the solvent system does not comprise free polyethylene glycol polymers. Preferred compositions are a single phase and homogeneous.

In one embodiment, the solvent system is substantially free of aqueous buffer.

In a second embodiment, the solvent system may comprise a single alkyl ether solvent. Such solvent may be selected from the group consisting of 1,2-dimethoxyoethane, di(ethylene glycol)methyl ether, diethylene glycol monoethyl ether and di(ethyleneglycol)diethyl ether. In a particular embodiment, the single alkyl ether solvent is diethylene glycol monoethyl ether.

Examples of the first binary solvent of the solvent system include, but are not limited to, diethylene glycol monoethylether or tetrahydrofurfuryl alcohol polyethyleneglycol ether. The first solvent may be, for example, present at a weight percent of between about 30% to about 70%. Examples of the second solvent of the solvent system include, but are not limited to, glycerol triacetate or propylene glycol. The second solvent may be, for example, present at a weight percent of between about 70% and about 30%. In some embodiments the second solvent is less capable of penetrating nasal mucosa than the first solvent.

The solvent system may, for example, consist essentially of the first solvent and the second solvent. In another embodiment, the solvent system may consist essentially of the first solvent, the second solvent, and an aqueous buffer solution (e.g., 10% (weight/weight) or less) and may further comprise additional components (e.g., an anti-oxidant).

The active drug, for example, the benzodiazepine, is typically present at a weight percent of between about 0.1% to about 20% and often between 0.1% and 10% often 0.25% to 6%.

In one embodiment, the first and second solvents are present in equal weight percents.

In addition to the components just described, pharmaceutical compositions comprising the benzodiazepine (e.g., clonazepam, diazepam or lorazepam) of the present invention, for example, for intranasal administration to a mammal, may further comprise one or more components including, but not limited to, a surfactant, anti-oxidant, pharmaceutically acceptable polymer, polyalcohol, lipid, mucosa penetration enhancing agent, colorant, flavoring or olfactory agent, anesthetic agent, co-solvent, and agent to adjust osmolarity.

In preferred embodiments of the present invention, the pharmaceutical compositions of benzodiazepine (e.g., clonazepam, diazepam or lorazepam) are formulated to be sprayable, for example, from a manually actuated spray device, and at temperatures between −15° C. and 30° C.

In a second aspect, the present invention includes a pharmaceutical composition for intranasal administration of a benzodiazepine to a mammal, for example, a human. In this aspect, the solvent system may comprise a single alkyl ether solvent or a first solvent, comprising one or more component selected from the group consisting of diethylene glycol monoethylether and tetrahydrofurfuryl alcohol polyethyleneglycol ether, and a second solvent, comprising one or more component selected from the group consisting of glycerol triacetate or propylene glycol. The solvent system may further comprise an aqueous buffer solution (e.g., 10% (weight/weight) or less, wherein the pH of the aqueous buffer solution is between about pH 4 to about pH 7, more preferably between about pH 4 to about pH 6.5). In preferred embodiments, there is a caveat that the solvent system does not comprise free polyethylene glycol polymers. The pharmaceutical compositions of the present invention for transmucosal administration of a benzodiazepine also comprise a therapeutically effective amount of the benzodiazepine. Typically, the composition is a single phase and homogeneous. In one embodiment of the benzodiazepine is lorazepam, in another embodiment it is diazepam.

In one embodiment, the solvent system is a binary solvent system, that is, a solvent system consisting essentially of two solvents. Such binary solvent systems may be, for example, substantially free of an aqueous component. In some embodiments of the present invention, the first solvent consists essentially of diethylene glycol monoethylether or tetrahydrofurfuryl alcohol polyethyleneglycol ether. The first solvent may be present at a weight percent of, for example, between about 30% to about 70%. In some embodiments, the second solvent consists essentially of glycerol, triacetate or propylene glycol. The second solvent may be present, for example, at a weight percent of between about 70% and about 30%. In another embodiment the pharmaceutical composition may include a single alkyl ether solvent such as diethylene glycol monoethyl ether Typically, the benzodiazepine is present at a weight percent of between about 0.1% to about 20%, more preferably at a weight percent of between about 0.1% to about 10%, more preferably at a weight percent of between about 0.25% to about 6%. In yet a further embodiment, the solvent system consists essentially of the first solvent and the second solvent. In another embodiment, the solvent system consists essentially of the first solvent, the second solvent, and an aqueous buffer solution (e.g., 10% (weight/weight) or less). The aqueous buffer may further comprise one or more additional components, for example, an anti-oxidant and/or surfactant.

In some embodiments of this aspect of the present invention, the first and second solvents are present in equal weight percents.

The pharmaceutical compositions of the present invention for intranasal administration of a benzodiazepine to a mammal may include further components, for example, less than about 10% (weight/weight) of one or more components including, but not limited to, a surfactant, anti-oxidant, pharmaceutically acceptable polymer, polyalcohol, lipid, mucosa penetration enhancing agent, colorant, flavoring agent, anesthetic agent, co-solvent, and agent to adjust osmolarity.

Examples of suitable pharmaceutically acceptable polymers include, but are not limited to, hydroxypropylmethyl cellulose, hydroxyethyl cellulose, hydroxypropyl cellulose, polyvinyl pyrrolidone, carboxymethyl cellulose, polyvinyl alcohol, sodium alginate, xanthane gum, tragacantha, guar gum, acacia gum, arabic gum, polyacrylic acid, methylmethacrylate copolymer, carboxyvinyl copolymers, and combinations thereof.

Surfactants useful in the practice of the present invention are typically, but not exclusively, non-ionic. Examples of suitable surfactants include, but are not limited to, TWEEN (i.e., polyoxyethylene sorbitan fatty acid ester), an alpha-hydro-omega-hydroxypoly(oxyethylene) poly(oxypropylene)poly(oxyethylene) block copolymer, a polyoxyethylene alkyl ether, a polyoxyethylene castor oil derivative, and combinations thereof.

Examples of suitable polyalcohols include, but are not limited to, glycerol, propylene glycol, glycerol monoesters with fatty acids, and combinations thereof. In preferred embodiments, the compositions of the present invention do not include free polyethlylene glycol polymers.

Examples of suitable solublizing agent agents include, but are not limited to, lipids (e.g., fats, oils, waxes, sterols, triglycerides, and combinations thereof).

The compositions of the present invention may further comprise a mucosal penetration enhancing agent. Examples of mucosal penetration enhancing agents include, but are not limited to, N-methyl-2-pyrrolidone, 2-pyrrolidone, propylene glycol, dimethylformamide, dimethyl sulfoxide, caprolactam, oleic acid, decylmethylsulfoxide, 1-dodecylazacycloheptan-2-one, isopropyl myristate, hexamethylene palmitamide, hexamethylene lauramide, aliphatic acids, esters, and combinations thereof.

Antioxidants typically provide enhanced stability to the composition as a whole and/or specifically contribute to stability of the active agent (e.g., the benzodiazepine). Addition of anti-oxidants may serve to protect the benzodiazepine from oxidative damage in some embodiments of the present invention. Accordingly, the compositions of the present invention may further comprise an anti-oxidant (e.g., edetic acid or sodium edetate, butylhydroxytoluene, propyl gallate, sodium metabisulfite, butylhydroxyanisole, tocopherols, and combinations thereof), in particular the antioxidant may be butylhydroxytoluene (BHT) at concentrations of 100-300 ppm more often 500-2000 ppm.

Further, one or more additional components may be added to the compositions of the present invention. Such additional components will be apparent to one of ordinary skill in the art in view of the teachings of the present specification. Such further components include, but are not limited to, a colorant, flavorant, and anesthetic agent.

In preferred embodiments, the benzodiazepine compositions of the present invention are formulated to be sprayable, for example, using a manually or electronically actuated spray device or a passive device that is actuated by the patient's act of inhalation. For sprayable compositions that are intended for delivery to the nasal cavity of a mammal, the composition may be used at a unit therapeutic dose of between about 50 μL and 300 μL, often between 25 μL and 150 μL and more preferably at a unit therapeutic dose of about 100 μL.

A therapeutically effective amount of clonazepam in the compositions of the present invention may be, for example, between about 0.1 mg and about 5.0 mg per unit dose, more preferably between about 1.0 mg and about 4.0 mg per unit dose. A therapeutically effective amount of lorazepam in the compositions of the present invention may be, for example between about 0.5 mg and about 10.0 mg per unit dose, more preferably between about 1.0 mg and about 5.0 mg per unit dose. A therapeutically effective amount of diazepam in the compositions of the present invention may be, for example between about 1.0 mg and about 40.0 mg per unit dose, more preferably between about 2.0 mg and about 10.0 mg per unit dose.

Some exemplary formulations of clonazepam compositions of the present invention are presented in Example 7, Table 20. In the example, methods of making the compositions are also described.

A third aspect of the present invention relates to a pharmaceutical composition comprising a benzodiazepine for transmucosal administration to a mammal, wherein the composition is characterized by $T_{max}$ of the benzodiazepine, after a single intranasal administration, and bioavailability of the benzodiazepine. In one embodiment, the composition is characterized by (i) a $T_{max}$ of the benzodiazepine, after a single intranasal administration, of no more than 2 hours and (ii) a bioavailability of the benzodiazepine, after a single intranasal administration, of no less than about 30% of the bioavailability of an equivalent dose of the benzodiazpine delivered orally. In other embodiments, the $T_{max}$ is less than or equal to 30 minutes and the bioavailability is greater than or equal to 55% of the bioavailability of orally delivered benzodiazepine. Exemplary $T_{max}$ and bioavailability data for some embodiments of the present invention are presented herein below in Example 5, Tables 12A and 12B, FIG. 5 and Example 14 $T_{max}$ may be less than or equal to 2 hours or less than or equal to 1 hour or less than or equal to 30 minutes or less than 15 minutes.

A fourth aspect of the present invention relates to a pharmaceutical composition comprising the benzodiazepine for transmucosal administration to a mammal, wherein the composition is characterized by $C_{max}$ of the benzodiazepine, after a single intranasal administration, and bioavailability of the benzodiazepine. In one embodiment, the composition is characterized by (i) a $C_{max}$ of the benzodiazepine, after a single intranasal administration, of at least about 75% of the $C_{max}$ of an equivalent dose of clonazepam delivered orally, and (ii) a bioavailability of the benzodiazepine, after a single intranasal administration, of no less than about 30% of the bioavailability of an equivalent dose of the benzodiazepine delivered orally. Exemplary $C_{max}$ and bioavailability data for some embodiments of the present invention are presented herein below in Example 5, Tables 12A and 12B, and FIG. 5. In other embodiments, the $C_{max}$ of intranasally delivered benzodiazepine is greater than or equal to 75% or greater than or equal to 80% of orally delivered benzodiazepine, or may be greater than or equal to 90% of the $C_{max}$ of the orally delivered benzodiazepine. In further embodiments the bioavailability is greater than or equal to 30% or greater than or equal to 40% of the bioavailability of orally delivered benzodiazepine or greater than 55% of orally delivered benzodiazepine.

A fifth aspect of the present invention relates to a pharmaceutical composition comprising a benzodiazepine for intranasal administration to a mammal, wherein the composition is characterized by a ratio of the AUC of the benzodiazepine, after a single intranasal administration, ($AUC_{in}$) to the AUC of an equivalent dose of the benzodiazepine delivered orally ($AUC_{oral}$) calculated for 24 hours after administration. In one embodiment, the composition is characterized by (i) a ratio of the AUC of a benzodiazepine, after a single intranasal administration, ($AUC_{in}$) to the AUC of an equivalent dose of the benzodiazepine delivered orally ($AUC_{oral}$) of at least about $AUC_{in}:AUC_{oral}=1:3.3$, wherein the AUC values are determined over the same time period (for example, 24 hours for human subjects). Exemplary AUC data for some embodiments of the present invention are presented herein below in Example 5, Tables 12A and 12B, FIG. 5 and Example 14. $AUC_{in}$ $AUC_{oral}$ can be at least about 1:3.3 or often at least about 1:2.5 or 1:1.8.

In addition to pharmaceutical compositions comprising a benzodiazepine for transmucosal administration to a mammal, the present invention further includes a method for administering an active agent (e.g., a benzodiazepine) to a mammal in need thereof. In the method, the benzodiazepine is delivered to the mammal's bloodstream by crossing the nasal mucosa of the mammal and entering the blood stream. The benzodiazepine may be delivered transmucosally using dosage forms described herein. The benzodiazepine may be administered to a mammal to treat a variety of conditions including, but not limited to, depression, panic disorders (including acute panic attacks), muscle spasms, insomnia, and seizures (including seizure clusters). The benzodiazepine compositions of the present invention may be self-administered or administered by a second party, for example, a health care professional, a family member, or significant other.

In one embodiment, the compositions of the present invention are used to treat a mammal suffering seizure clusters by, for example, delivery of a benzodiazepine to the mammal's bloodstream via nasal mucosa of the mammal, wherein the benzodiazepine is delivered in an intranasal dosage form of the present invention. Administration of the compositions of the present invention may be performed, for example, at the onset of the symptoms of seizures. One or more unit doses may be administered to the mammal. In preferred embodiments the mammal is a human.

The present invention also includes methods of manufacturing a benzodiazepine composition useful for intranasal delivery of a benzodiazepine. A general method of making exemplary compositions of the present invention is described herein below in Example 7. Typically, the method includes mixing the solvent system and the benzodiazepine under conditions to provide a single-phase, homogeneous solution suitable for intranasal administration of the benzodiazepine. The benzodiazepine may be first dissolved in the solvent in which it has higher solubility, for example, the first solvent. The second solvent may be added with stirring. Mixing of the solution compositions of the present invention may be carried out under conditions that reduce exposure of the benzodiazepine to oxidative conditions, for example, by mixing under nitrogen or in a reduced oxygen environment.

After preparation of the solution compositions of the present invention, the solution may be dispensed into one or more containers (e.g., a unit dose container or a multiple dose container). The container may be a manually actuated spray device or a spray device wherein the contents are maintained under pressure and released by depressing an actuator or a device that is actuated by the patient's act of inhalation.

Typical unit doses delivered by these spray devices for intranasal delivery are between about 50 μL to about 300 μL, often 25 μL to about 150 μL, preferably a volume of about 100 μL, but for certain devices can be up to 5 mL. The spray pattern and plume geometry of the compositions as delivered from the spray device are suitable for intranasal delivery to a mammal (e.g., human). Parameters related to sprayability and viscosity of solvent matrices (solvent systems) related to the practice of the present invention are described in Example 6.

2.1.2 Manufacturing and Packaging

Preparation of the Benzodiazepine Compositions of the Present Invention, for example, formulated for intranasal administration, may be performed following the teachings of the present specification in view of teachings known to those of ordinary skill in the art. For example, according to the present invention, the benzodiazepine compositions may be prepared generally as follows. A solvent is selected in which the selected benzodiazepine is soluble, for example, clonazepam is very soluble in diethylene glycol monoethylether and/or tetrahydrofurfuryl alcohol polyethyleneglycol ether. The desired amount of the benzodiazepine is added with stirring to obtain a substantially single phase, substantially homogeneous solution. A second solvent (for example, triacetin and/or propylene glycol and/or an aqueous buffered solution) may then be added to the solution comprising the first solvent and the benzodiazepine. The mixture is stirred to obtain a substantially single phase, substantially homogeneous solution. Additional components are typically first dissolved in the solvent in which they have the highest solubility.

As another example, the desired amount of the benzodiazepine may be dissolved in a solvent (e.g., diethylene glycol monoethylether and/or tetrahydrofurfuryl alcohol polyethyleneglycol ether) and stirred to obtain a substantially single phase, substantially homogeneous solution. A second solvent, for example, an aqueous buffered solution may be prepared with additional components. Such additional components may include, but are not limited to, anti-oxidant (e.g., sodium metabisulfite) and/or surfactant (e.g., TWEEN). The buffering agent (or buffering system) should be able to maintain the pH of the formulation in the target range. After the addition of some buffering agents, further adjustment of pH may be desirable by addition of a second agent to achieve pH values in the target range. In view of the fact that the compositions of the present invention are directed to pharmaceutical use, the buffering agent or system should not be substantially irritating to mucosal tissue to which the composition is being applied. Buffering agents include organic and non-organic buffering agents. Exemplary buffering agents include, but are not limited to, phosphate buffer solutions, carbonate buffers, citrate buffers, phosphate buffers, acetate buffers, sodium hydroxide, hydrochloric acid, lactic acid, tartaric acid, diethylamine, triethylamine, diisopropylamine, and aminomethylamine. Ultimately buffering agents are used at a concentration to achieve the desired target pH range; accordingly weight percent amounts of buffering agents may vary as may be determined by one of ordinary skill in the art in view of the teachings of the present specification.

The aqueous buffered solution (possibly comprising further components) is stirred to obtain a substantially single phase, substantially homogeneous solution. Aqueous solutions may be degassed; but degassing is not typically necessary. The aqueous buffered solution is then slowly added to the first solvent in which the benzodiazepine was dissolved to obtain a substantially single phase, substantially homogeneous solution.

As another example, the benzodiazepine may be dissolved in a first solvent (for example, diethylene glycol monoethylether and/or tetrahydrofurfuryl alcohol polyethyleneglycol ether). A second solvent may be added (for example, triacetin and/or propylene glycol), and may be followed by the addition of, for example, an aqueous buffered solution, with or without additional components.

Mixing may be carried out under normal conditions or under a slight vacuum and/or nitrogen blanketing.

The methods of manufacturing of the present invention may further include dispensing compositions of the present invention into appropriate containers. The compositions of the present invention may be packaged, for example, in unit dose or multi-dose containers. The container typically defines an inner surface that contains the composition. Any suitable container may be used. The inner surface of the container may further comprise a liner or be treated to protect the container surface and/or to protect the composition from adverse affects that may arise from the composition being in contact with the inner surface of the container. Liners or coating material are typically substantially impermeable to the composition and typically to the individual components of the composition.

A number of types of suitable containers commercially available and known in the art, for example, as manufactured by Pfeiffer of America, Princeton, N.J. (e.g., U.S. Pat. Nos. 5,584,417, 6,705,493, 6,446,839, 6,478,196), and Valois of America Inc., Greenwich, Conn. (e.g., U.S. Pat. Nos. 5,328,099, 6,742,677, 7,080,759).

Containers/Delivery systems for the compositions of the present invention may include unit dose or multi-dose containers providing, for example, a fixed or variable metered dose application. Multi-dose containers include, but are not limited to, a metered dose aerosol, a stored-energy metered dose pump, or a manual metered dose pump. In preferred embodiments, the container/delivery system is used to deliver metered doses of the compositions of the present invention for application to the nasal cavity of a subject. Metered dose containers may comprise, for example, an actuator nozzle that accurately controls the amount and/or uniformity of the dose applied. The delivery system may be propelled by, for example, a pump pack or by use of propellants (e.g., hydrocarbons, hydro fluorocarbons, nitrogen, nitrous oxide, or carbon dioxide). Devices such as those sold by Kurve® Technology described as ViaNase™ atomizers, which allow for electronic dosing and nasal cavity saturation may be used. Further, devices such as passive devices sold by OptiNose (Oslo, Norway) may be actuated by the patient's inhalation. In preferred embodiments of the present invention, the container is a single-use, unit-dose, manually actuated spray device.

Example 6 describes methods to evaluate sprayability and viscosity of the benzodiazepine formulations of the present invention. The results obtained from experiments performed in support of the present invention demonstrated that the benzodiazepine formulations described herein are suitable for intranasal delivery.

Nasal tissue comprises a single epithelial layer and has a limited area suitable for absorption of drugs delivered intranasally. Typically the nasal tissue area in adult humans is about 20 cm$^2$. Volume per unit dose of compositions delivered intranasally is typically limited to between about 25 µl and about 150 µl, per nostril, and if delivered to 2 nostrils, a unit dose may be 50 µL to 300 µL. A unit dose of about 100 µL is suitable for many applications which dose may be delivered 50 µL per nostril or 100 µL in one nostril. A preferred droplet size distribution for intranasal delivery is typically in the range of about 10 µm to about 50 µm, but may vary as long as sufficient transnasal absorption of the active drug is effected.

In a preferred embodiment, airless packaging with excellent barrier properties is used to prevent oxidation of the benzodiazepine, for example, airless single-dose manually actuated spray devices. Accurate dosing from such pumps ensures reproducibility of dose.

2.1.3 Further Dosage Forms

In another aspect of the present invention, benzodiazepines are delivered to mucosal tissue, for example, intranasally, using dry powder formulations. Such dry powder formulations may comprise micronized particles of a selected benzodiazepine (e.g., clonazepam).

Intranasal administration of benzodiazepines may be accomplished, for example, as described herein, by solublizing a selected benzodiazepine in a suitable solvent system then using an intranasal spray device intended for use with a liquid form. Examples of liquid forms useful for such applications include, but are not limited to, an emulsion, a suspension, or a true solution. Due to the highly lipophilic nature of the benzodiazepines a combination of surfactants, strong solublizing solvents, and carrier solutions are often used. An alternative to such liquid forms is a dry powder formulation of benzodiazepine (e.g., diazepam, lorazepam, midazolam, clonazepam, and the like) that may be administered intranasally as a dry powder or a blend.

Intranasal delivery of particulate benzodiazepines would likely result in an acceptable delivery profile for benzodiazepines due to the intrinsic permeation properties of the substances. Benzodiazepines tend to be highly lipophilic, thus compatible with adsorption to and absorption by mucosal tissues. Particle sizes ranging from about 5 µm to about 20 µm would allow a dry-powder dispensing device to deliver sufficient quantities of selected benzodiazepines to effect pharmacological action in a short time frame. Methods of preparing dry powders of benzodiazepines with suitable size distribution (e.g., micronized powders) include, but are not limited to, anti-solvent precipitation, fluid bed drying, spray drying, size sorting, as well as combinations thereof.

Benzodiazepine, for example, clonazepam, dry powders may also be blended with suitable carriers for nasal administration to improve wetting, mucoadhesion and permeability (see, for example, European Patent Application Nos. EP 1587514A1, EP1652518A1, EP 0324725B1, for examples of such carriers). In this aspect, benzodiazepines may be formulated in an ordered mixture where the core is an inert carrier such as a sugar and the surface is a combination of mucoadhesives and drug.

Advantages of this dry powder drug delivery approach include excellent stability and possibly greater intranasal residence time leading to improved drug uptake. A suitable dry powder intranasal delivery system may be used.

Dry powder formulations of the present invention may employ microparticles of a benzodiazepine of less than about 15-20 microns, more preferably of between about 5 and about 10 microns. The microparticles of the benzodiazepine may be combined with carrier particles as described above. Preferably, a mucoadhesion promoting agent is added to the carrier particles. The mucoadhesion promoting agent is effective in making the benzodiazepine adhere to the nasal mucosa. The mucoadhesion promoting agent is typically present on the surface of the carrier particles, but it may also be present within the particles.

In one embodiment, the carrier particles contain from about 0.1 to about 30 weight percent, preferably between about 1 to about 20 weight percent, of mucoadhesion agents, based on the total weight percent composition of the dry composition. The preferred mucoadhesive agent is typically a polymeric substance, preferably having an average molecular weight above 5,000 (weight average). The hydration of mucoadhesive agents also makes them useful as absorption enhancers according to the invention.

Carrier particle size is typically from about 50 µm to about 800 µm, preferably from about 50 µm to about 500 µm. Exemplary carrier particle substances include, but are not limited to, carbohydrates, such as sugar, mannitol and lactose, or pharmaceutically acceptable inorganic salts, such as sodium chloride or calcium phosphate, or mixtures thereof.

Dry powder compositions of the present invention may include a pharmaceutically acceptable surfactant (such as those described above). The increased wetting effect of the surfactant in the composition can enhance the hydration of the carrier particles. This enhanced hydration may result in faster initiation of mucoadhesion. Typically, the surfactant is in a finely dispersed form and intimately mixed with the clonazepam. The amount of surfactant may be, for example, from about 0.5 to about 5 weight percent of the dry composition, and preferably from about 0.5 to about 3 weight percent.

A variety of polymers known in the art can be used as mucoadhesive agents and examples are listed above included in the list of pharmaceutically acceptable polymers. The mucoadhesive polymers are typically hydrophilic, water-dispersible, or hydrophilic and water-dispersible. The ability of the polymer to swell in the presence of water is sometimes desirable. Mucoadhesiveness of substances can be determined in vitro, for example, as described by Sala, G., et al., Proceed. Int. Symp. Contr. Release. Bioact. Mat. 16:420 (1989).

Devices for the intranasal delivery of fine, powdered compositions are known in the art (for example, U.S. Pat. Nos. 6,948,492, 6,824,080, 6,752,147, 6,715,485, 6,488,648, 5,901,703, 4,227,522, 4,192,309, 4,105,027) and may be used for delivery of the powdered compositions of the present invention comprising a benzodiazepine.

These dosage forms may be used in similar methods of use/treatment to those described above.

These aspects are described herein below with reference to clonazepam as an exemplary benzodiazepine. These examples are not intended to be limiting. Other objects of the invention may be apparent to one of ordinary skill upon reviewing the teachings of the specification and preferred embodiments of the invention described herein.

EXPERIMENTAL

As is apparent to one of skill in the art, various modifications and variations of the above embodiments can be made without departing from the spirit and scope of this invention. Such modifications and variations are within the scope of this invention. Some of the above-described aspects of the present invention are described herein below with reference to clonazepam as an exemplary benzodiazepine.

The following examples are put forth so as to provide those of ordinary skill in the art with a complete disclosure and description of how to make and use the devices, methods, and formulae of the present invention, and are not intended to limit the scope of what the inventors regard as the invention. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

The compositions produced according to the present invention meet the strict specifications for content and purity required of pharmaceutical products.

Materials and Methods

A. Pharmaceuticals and Reagents: The pharmaceuticals and reagents used in the following examples can be obtained from commercial sources, for example, as follows: active drug, e.g., clonazepam (from Lake Chemicals, India, or F.I.S.—Fabbrica Italiana Sintetici SpA, Vicenza, Italy) where delivered orally, the tablet is half of a Rivotril® 2 mg scored tablet (Hoffman-La Roche, New Jersey) diazepam and lorazepam (from Cambrex Profarmaco, Milan, Italy); penetration enhancers and solvents (e.g., diethylene glycol monoethylether, also called TRANSCUTOL®, from Gattefossé Corporation, Paramus, N.J.); antioxidants (e.g., butylhydroxytoluene (BHT), butylhydroxyanisole (BHA), sodium metabisulfite, from Sigma-Aldrich Corporation, St. Louis, Mo.); pharmaceutically acceptable polymers (e.g., hydroxypropyl cellulose, from Hercules, Inc., Wilmington, Del.); excipients, soublizers, and solvents, e.g., triacetin (also called glycerol triacetate or 1,2,3-Propanetriol, triacetate) from Mallinckrodt Baker, Inc., Phillipsburg N.J.; propylene glycol, from Apotekproduksjon, Norway; GLYCOFUROL™ (also called ethoxylated furanyl alcohol or tetrahydrofurfuryl alcohol polyethyleneglycol ether) and similar ethoxylated tetrahydrofurfuryl alcohols, from Agrar, Italy); and standard pharmaceutical and chemical reagents (e.g., colorants, solvents, and surfactants, from Sigma-Aldrich Corporation, St. Louis, Mo., Fisher Scientific, UK, and Merck, Germany: for example, propylene glycol, PEG 0.200 (ICI Americas Inc., Bridgewater N.J.) and TWEEN® 20, from Merck, Germany; Citric acid from Riedel-de-Haen, Germany; triacetin from Abitec, USA; and water (WFI) from Fresenius Kabi, Norway). Analytical reagents are also available from a number of commercial sources, for example, citric acid, from Acros Organics, UK; hydrochloric acid, acetonitrile (HPLC grade), methanol (HPLC grade), orthophosphoric acid, potassium chloride, potassium hydrogen phthalate, potassium dihydrogen orthophosphate, ethanol, from Fisher Scientific, UK; and disodium hydrogen phosphate dihydrate, sodium dihydrogen phosphate, from Merck, Germany.

B. HPLC Analytical Methods: The HPLC system for detection of clonazepam was as follows: Waters 2487 Dual λ Absorbance Detector, Waters 600 Controller, Waters 717 plus Autosampler, Waters Millennium Chromatograph Manager Software (Waters Corporation, Milford, Mass.); Column, Chromolith Performance RP-18e 100×4.6 mm, and Guard Column, Chromolith Guard Cartridge RP-18e 5×4.6 mm (Merck KgaA, Frankfurt, Germany); Detection, λ=220 nm; Sample Temperature, 20±2° C.; Column Temperature, Ambient temperature; Flow Rate, 2.0 mL/min; Mobile Phase, Isocratic, Mobile Phase, $KH_2PO_4$ 35 mM in deionized water (pH 2.1 adjusted with orthophosphoric acid): acetonitrile—70:30; Injection Volume, 100 µL; Run Time, 10-20 min; and Needle Wash, 90:10 (methanol:water).

The limit of detection (LOD) and quantification (LOQ) were calculated according to Equations 1 and 2:

$$LOD = (3.3 * STEYX)/S \quad \text{(Equation 1)}$$

$$LOQ = (10 * STEYX)/S \quad \text{(Equation 2)}$$

where, STEYX=the standard deviation of the y-intercepts of regression lines, obtained from the respective calibration curve and S=the gradient of the calibration curve.

Preliminary stability studies of drug standard solution were performed in phosphate buffered saline (PBS) containing 10% ethanol. In parallel, the stability of drug in various buffer pH values (pH 2 to 8) was also investigated. Because clonazepam was poorly soluble in water, 10% ethanol was added to each buffer system in order to aid solubility. The stability of drug in each buffer system was determined over a period of 72 hours at 37° C. and 2-8° C.

The preparation of buffers was as follows. The preparation of buffers pH 2 to 4 are summarized in Table 1.

TABLE 1

| | Composition of buffers pH 2 to 4 | | | | |
|---|---|---|---|---|---|
| Buffer pH | Potassium chloride (mL) | Potassium hydrogen phthalate (mL) | Hydrochloric acid 1M (mL) | Deionized water (mL) | Actual pH recorded |
| 2 | 50 | 0 | 7.8 | 142.2 | 2.11 |
| 3 | 0 | 50 | 15.7 | 134.3 | 3.17 |
| 4 | 0 | 50 | 0.1 | 149.9 | 3.98 |

Potassium chloride solution was prepared by adding 14.9 g of solid into a 1 L volumetric flask and made up to volume with deionized water. Potassium hydrogen phthalate solution was prepared by adding 40.8 g of solid into a 1 L volumetric flask and made up to volume with deionized water.

The preparation of buffers pH 5 to 7 is summarized in Table 2.

TABLE 2

Composition of buffers pH 5-7

| Buffer pH | Citric acid (mL) | Sodium dihydrogen phosphate (mL) | Deionized water (mL) | Actual pH recorded |
|---|---|---|---|---|
| 5 | 24.3 | 25.7 | 50 | 5.2 |
| 6 | 16.9 | 33.1 | 50 | 6.09 |
| 7 | 6.5 | 43.6 | 49.9 | 6.98 |

Citric acid solution was prepared by adding 21.01 g of solid into a 1 L volumetric flask and made up to volume with deionized water. Sodium dihydrogen phosphate solution was prepared by adding 13.8 g of solid into a 1 L volumetric flask and made up to volume with deionized water.

The preparation of buffer pH 8 is summarized in Table 3.

TABLE 3

Composition of buffers pH 8

| Buffer pH | Sodium dihydrogen phosphate (mL) | Disodium hydrogen phosphate (mL) | Deionized water (mL) | Actual pH recorded |
|---|---|---|---|---|
| 8 | 94.7 | 5.3 | 100 | 8.13 |

Disodium hydrogen phosphate dehydrate was prepared by adding 35.6 g of solid into a 1 L volumetric flask and made up to volume with deionized water. Sodium dihydrogen phosphate solution was prepared by adding 13.8 g of solid into a 1 L volumetric flask and made up to volume with deionized water.

The percentage drug recovered was calculated using Equation 3:

$$\% \text{ drug recovered} = (\text{drug concentration at } t=X/\text{drug concentration at } t=0) \times 100 \quad \text{(Equation 3)}$$

where, X=specific time point and temperature.

Following the stability studies, a suitable receiver fluid was developed in order to ensure that sink conditions for tested drug were such that the drug release was limited by the solubility of the drug in the receiver fluid. The saturated solubility (at 37° C.) for drug was performed in 3 solvent/co-solvent systems, namely, pH 6 buffer, 10% ethanol in pH 6 buffer and 20% ethanol in pH 6 buffer. Briefly, drug was saturated into different receiver fluid systems by adding excess drug and allowed to stir with a magnetic flea over a period of 2 h at 37° C. Each saturated solution was then filtered using a 0.2 µm syringe filter and the resultant solution was assayed via HPLC.

C. In vitro Permeation Methodology: In vitro permeation was carried out by standard methods (e.g., Franz, T. J., "Percutaneous absorption: on the relevance of in vitro data," J. Invest Dermatol 64:190-195 (1975); Franz, T. J., "The finite dose technique as a valid in vitro model for the study of percutaneous absorption in man," In: Skin: Drug Application and Evaluation of Environmental Hazards, Current Problems in Dermatology, vol. 7, G. Simon, Z. Paster, M Klingberg, M. Kaye (Eds), Basel, Switzerland, S. Karger, pages 58-68 (1978)).

Freshly excised sheep nasal mucosa was used and prepared following a standard protocol. The excised sheep nasal mucosa was cleaned by rinsing with de-ionized water and either used fresh or placed flat over a filter paper and stored frozen until used.

(i) Drug recovery, degradation and binding to nasal sheep mucosa: The effect of drug recovery, degradation and binding to sheep nasal mucosa was determined. Briefly, a known surface area (approx. 1 cm$^2$) of sheep nasal mucosa was added into a glass vial containing a known concentration (10 µg/mL) of each drug prepared in the receiver fluid (10% ethanol in pH 6 buffer). The content of the vial was allowed to equilibrate at 37° C. over a period of 48 h. At 24 h intervals, a sample was removed and assayed via HPLC. The percentage of drug recovered was calculated using Equation 4:

$$\% \text{ drug recovered} = (\text{drug concentration at } t=Y/\text{drug concentration at } t=Z) \times 100 \quad \text{(Equation 4)}$$

where, Y=specific time point at 37° C. (in the presence of nasal sheep mucosa); and Z=specific time point at 37° C. (in the absence of nasal sheep mucosa).

(ii) Dosing and Sample Collection—Franz cell studies: Individually calibrated Franz cells with an average surface area and volume of approximately 0.6 cm$^2$ and 2 mL, respectively, were employed to determine the permeation characteristics of drug. The nasal sheep mucosa was mounted between the two halves of the Franz cell with the mucosal side facing the donor compartment. The receptor compartment was filled with receiver fluid, stirred constantly with a PTFE-coated magnetic follower driven by a submersible magnetic stirrer bed and maintained at 37° C. in a water bath. Approximately 1 mL (infinite dose) of saturated drug solution was placed into the donor compartment and covered with PARA-FILM® (Pechiney Plastic Packaging, Inc., Chicago, Ill.) throughout the study. Following the application of the drug solution, the receiver fluid (200 µL) was removed from the receptor compartment via the sampling arm after sampling times (t=1, 2, 3, 4, 5, 6 and 7 h) and analyzed via HPLC. Each sample removed was replaced by an equal volume of fresh pre-warmed (37° C.) receiver fluid. A total of eight repetitions (n=8) were performed on the drug solution and a single control experiment where no drug was present in the donor compartment was also performed.

D. Neurocognitive Tests: The Cognitive Drug Research (CDR) computerized assessment system is specifically designed to evaluate the effects of compounds on the quality of cognitive functioning in subjects and patients in all phases of clinical development. The CDR system is a widely used computerized cognitive assessment system (see, for example, Ebert U, et al., "Pharmacokinetics and pharmacodynamics of scopolamine after subcutaneous administration," *Journal of Clinical Pharmacology* 38: 720-726 (1998); Harrington F, et al., "Cognitive Performance in Hypertensive and Normotensive Older Subjects," *Hypertension* 36: 1079-1082 (2000); Preece A W, et al., "Effect of a 915-MHz simulated mobile phone signal on cognitive function in man," *International Journal of Radiation Biology* 75: 447-456 (1999); and Walker M P, et al., "Quantifying fluctuation in Dementia with Lewy Bodies, Alzheimer's disease and vascular dementia," *Neurology* 54: 1616-1625 (2000)) and has been used to evaluate a diverse range of pharmaceutical compounds.

E. Electroencephalography (EEG) Methods: Drug and placebo are administered, for example, at a five-minute intravenous (i.v.) infusion. During 15 minutes following the beginning of the administration EEG is registered. The EEG is registered again at 30, 60, 90, 120, and 180 minutes. Subjects are typically in a quiet laboratory (soundproof and electrically shielded room). During acquisition of EEG measurements subjects recline in an armchair. Usually twenty-eight EEG leads (issued, for example, from a 10-20 system; Jasper, H. H., et al., "Studies of clinical and electrical responses to deep temporal stimulation in men with some considerations of functional anatomy," Res Publ Assoc Res Nerv Ment Dis. 36:316-34 (1958); Japser, H. H., "Progress and problems in brain research," J Mt Sinai Hosp N Y. 25(3):244-53 (1958)) are used for recording. An ear linked reference, as well as four artifact channels (detection of eye movement, muscle activity, and other potentials for artifacts) may be used. Silver-plated disc electrodes are attached to subject's scalp, for example, with quick drying collondion. Impedance (for example, of 2000-5000 ohms) is checked before each recording session. A calibration signal is used, before each subject is tested, in order to adjust all the recorded leads thus allowing the construction of EEG or event-related-potentials (ERP) maps. EEGs are taken under resting recording conditions (i.e., subjects are asked to relax with their eyes closed). An example of data analysis used is the method of Dago, et al. (Dago, K T, et al., "Statistical Decision Tree: a tool for studying pharmaco-EEG effects of CNS-active drugs," Neuropsychobiology, 29(2):91-6 (1994)) which involves a statistical comparison of data obtained during active treatment versus placebo treatment. Typically, topographic mapping of mean EEG parameters and statistical evaluation of treatment effects is carried out in a selected number of healthy volunteers.

Example 1

Absorption of Benzodiazepines Through Nasal Mucosa In Vitro

The following experiments, performed in support of the present invention, demonstrate the ability of benzodiazepines to penetrate nasal mucosa. The permeation of saturated solutions of clonazepam, diazepam and lorazepam across sheep nasal mucosa in vitro is described herein below.

HPLC detection of clonazepam showed the principal eluted peak had a retention time of 7.5 minutes; for lorazepam 7.3 minutes; and for diazepam 14 minutes. Calibration curves for clonazepam were constructed between 0.2 to 10 μg/mL with appropriate replicates to ensure repeatability and linearity. The saturated solubility for clonazepam in the receiver solution (10% ethanol in buffer pH 6, see Materials and Methods) was 29.32 μg/mL; for lorazepam, 125.79 μg/mL; and for diazepam 129.47 μg/mL. In buffer pH 6 the saturated solubility for clonazepam was 13.66 μg/mL; for lorazepam 78.49 μg/mL; and diazepam 62.93 μg/mL and in 20% ethanol in buffer pH6 the saturated solubility for clonazepam was 82.28 μg/mL; for lorazepam 308.92 μg/mL; and for diazepam was 362.06 μg/mL.

Standards were prepared in receiver fluid (10% ethanol in buffer 6). Although the solubility of drug in 10% ethanol/buffer pH 6 was not extremely high, it was selected over the 20% ethanol/buffer pH 6 because it was considered that the latter may perturb the nasal mucosa. It should also be noted that although the saturated solubility was determined at 37° C., the filtration of the saturated system was performed at room temperature. The filtration at room temperature was performed as quickly as possible to minimize any drug precipitation as the temperature dropped from 37° C. during filtration.

The linearity for the calibrations was found to be excellent ($r^2$ greater than or equal to 0.999). The limit of detection (LOD) and quantification (LOQ) for clonazepam was shown to be LOD (μg/mL) 0.269 and LOQ (μg/mL) 0.898; for lorazepam LOD (μg/mL) 0.376 and (μg/mL) 1.252; and for diazepam LOD (μg/mL) 0.204 and LOQ (μg/mL) 0.681.

Preliminary stability studies were performed in 10% ethanol in phosphate buffer (PBS). The data are summarized in Table 4 for drug stability studies at 2-8° C. and 37° C. in the presence of nasal sheep mucosa.

TABLE 4

Preliminary stability data for standards prepared in 10% ethanol/PBS

| Drug | Conc (μg/mL) | Ave % recovery at 2-8° C. | | | Ave % recovery at 37° C. | | |
| --- | --- | --- | --- | --- | --- | --- | --- |
| | | T = 24 h | T = 48 h | T = 72 h | T = 24 h | T = 48 h | T = 72 h |
| Lorazepam | 10.02 | 100.69 ± 0.09 | 99.46 ± 0.12 | 94.25 ± 0.59 | 97.50 ± 0.42 | 88.68 ± 0.25 | 68.37 ± 1.33 |
| Diazepam | 9.94 | 102.27 ± 0.17 | 101.77 ± 0.12 | 100.37 ± 0.31 | 102.76 ± 0.97 | 102.86 ± 0.50 | 99.72 ± 2.23 |
| Clonazepam | 9.96 | 100.21 ± 0.01 | 100.64 ± 0.17 | 105.16 ± 7.32 | 101.07 ± 0.65 | 101.86 ± 1.13 | 100.55 ± 0.77 |

The data clearly suggested that the benzodiazepines are stable at both temperatures over the 72 h period.

Following the preliminary stability study, the stability of prepared drug solution was repeated over a range of buffer pH values. The percent drug recovered as a result of drug stability or degradation is summarized in Table 5.

TABLE 5

Percentage (%) drug recovered from stability studies

| Drug | *Buffer pH | % recovery 2-8° C. | | | % recovery 37° C. | | |
| --- | --- | --- | --- | --- | --- | --- | --- |
| | | T = 24 h | T = 48 h | T = 72 h | T = 24 h | T = 48 h | T = 72 h |
| Lorazepam | 2 | 98.46 | 98.39 | 97.17 | 73.96 | 55.75 | 16.82 |
| | 3 | 99.67 | 93.17 | 98.84 | 88.76 | 68.71 | 43.08 |
| | 4 | 100.38 | 92.11 | 100.21 | 96.24 | 80.34 | 74.38 |
| | 5 | 99.83 | 98.41 | 100.25 | 97.89 | 90.29 | 84.38 |
| | 6 | 99.32 | 95.31 | 99.69 | 96.65 | 80.97 | 83.18 |
| | 7 | 99.27 | 94.32 | 99.79 | 95.41 | 80.23 | 77.72 |
| | 8 | 101.39 | 92.86 | 99.46 | 92.22 | 74.23 | 59.65 |

TABLE 5-continued

Percentage (%) drug recovered from stability studies

| Drug | *Buffer pH | % recovery 2-8° C. | | | % recovery 37° C. | | |
| --- | --- | --- | --- | --- | --- | --- | --- |
| | | T = 24 h | T = 48 h | T = 72 h | T = 24 h | T = 48 h | T = 72 h |
| Diazepam | 2 | 98.94 | 97.02 | 101.11 | 97.29 | 98.10 | 100.62 |
| | 3 | 100.38 | 98.13 | 99.95 | 101.00 | 100.61 | 100.33 |
| | 4 | 99.89 | 97.84 | 99.97 | 100.28 | 100.67 | 98.02 |
| | 5 | 98.95 | 98.11 | 98.24 | 99.84 | 100.70 | 100.32 |
| | 6 | 99.06 | 98.15 | 97.67 | 98.53 | 99.57 | 102.01 |
| | 7 | 98.30 | 97.15 | 96.34 | 98.98 | 99.21 | 102.10 |
| | 8 | 99.31 | 98.69 | 98.36 | 98.87 | 99.48 | 101.19 |
| Clonazepam | 2 | 90.08 | 73.18 | 55.30 | 57.97 | 55.51 | 53.07 |
| | 3 | 97.87 | 91.94 | 85.55 | 88.73 | 88.37 | 85.50 |
| | 4 | 99.54 | 98.88 | 99.37 | 98.72 | 100.09 | 101.91 |
| | 5 | 99.85 | 99.91 | 99.91 | 100.59 | 100.98 | 103.29 |
| | 6 | 100.41 | 100.32 | 100.43 | 100.34 | 100.59 | 103.14 |
| | 7 | 100.66 | 99.98 | 100.19 | 99.81 | 100.05 | 100.54 |
| | 8 | 99.59 | 99.30 | 99.40 | 96.76 | 96.42 | 91.47 |

*prepared in 10% ethanol

The data obtained confirmed that benzodiazepines appeared to be stable between pH 4-7 at the higher temperature over the 72 h period. Given that the duration of planned permeation studies was likely to be less than 24 hours and that the physiological pH of the nasal mucosa may vary between pH 5 to 6.5, buffer pH 6 was selected as the buffer of choice for the permeation studies.

In addition to the stability against heat degradation, the effect of drug binding or degradation in the presence of nasal sheep mucosa was also determined (Table 6).

TABLE 6

Percentage (%) drug recovered in the presence of nasal sheep mucosa at 37° C.

| | % recovery | | | | | |
| --- | --- | --- | --- | --- | --- | --- |
| | *Buffer pH 5 | | *Buffer pH 6 | | *Buffer pH 7 | |
| Drug | 24 h | 48 h | 24 h | 48 h | 24 h | 48 h |
| Lorazepam | 96.92 | 94.90 | 96.78 | 96.96 | 96.19 | 91.68 |
| Clonazepam | 97.78 | 96.45 | 97.47 | 97.14 | 99.30 | 97.78 |
| Diazepam | 97.64 | 95.62 | 98.02 | 124.68 | 97.61 | 94.68 |

*prepared in 10% ethanol

The data, presented as described in Equation 2 (Materials and Methods), were such that any loss in recovery would be as a result of the effect of the presence of nasal sheep mucosa but not heat degradation. The data generally suggested that some degree of binding or degradation (<10%) was apparent in the presence of nasal sheep mucosa for drug.

Preliminary permeation studies were performed as described above in the Materials and Methods section. Permeation achieved steady state, which suggested that drug permeation was not affected by the solubility of drug in receiver fluid (10% ethanol in pH 6 buffer). The data clearly showed steady state flux of the drug over a 24 h period.

Final permeation studies were performed over a 7 hour test period. The permeation characteristics of the drug in the preliminary study appeared to be closely similar to that in the final permeation study. FIG. 1 presents a graphic representation of the mean cumulative amount of the benzodiazepines permeated per unit area over a period of 7 h. The data suggested that permeation of the benzodiazepines were at steady state as demonstrated by the linear permeation rate of drug.

The HPLC methodology was shown to be "fit for purpose" with no interference peaks present at the same retention time as the drug peaks. Although the solubility study demonstrated that sink conditions did not apply throughout both permeation studies, nevertheless permeation achieved steady state for the benzodiazepines suggesting that the solubility of drug in the receiver fluid (10% ethanol in pH 6 buffer) was not rate limiting.

The preliminary stability data presented above suggested that the benzodiazepines were stable at 37° C. over 24 h in receiver fluid (10% ethanol in buffer pH 6). In addition, greater than 95% of drugs were recovered in the presence of nasal sheep mucosa at 37° C. over 48 h, suggesting that only a low degree of binding or degradation occurred.

The permeation characteristics for the benzodiazepines were found to be very similar in both preliminary and final study where steady state flux was observed. In conclusion, the data demonstrated that the benzodiazepines had acceptable stability in the context of use for intranasal administration, as well as acceptable permeation characteristic through nasal mucosa.

Example 2

Solubility in Solvent Matrices

The solubility of clonazepam in a number of neat solvents was determined using standard methods. The results are presented in Tables 7A and 7B.

TABLE 7A

Solubility of Clonazepam in Neat Solvents

| Matrix | Solubility (mg/mL) |
| --- | --- |
| PEG 300 | 37.0 |
| PEG 200 | 30.3 |
| propylene glycol | 3.4 |
| Triacetin | 5.8 |
| Glycofurol | 67.3 |
| Transcutol ® | 38.7 |
| Water | <0.1 |

From Table 7A it can be seen that Glycofurol was a good solvent for clonazepam and may therefore be useful for achieving target solubility of, for example, 10 to 20 mg/mL.

Further, the presence of Glycofurol may facilitate solubility in formulations solvents with lower clonazepam solubility, such as triacetin or propylene glycol. Transcutol® and PEG (polyethylene glycol) matrices also demonstrated high solubility.

The solubilities of several other benzodiazepines were measured in DEGEE (diethylene glycol monoethyl ether, transcutol) by the techniques of Example 1. Initially, 10 mg of the drug was loaded in the glass vial and 130-µL of DEGEE was added, and the samples were sonicated for 10 minutes. In the case of lorazepam and diazepam, the initial 10 mg went completely into solution, so another 10 mg was added to the vial prior to sonication again for 10 minutes. Samples were stored at −16° C. and 25° C. overnight, and centrifuged (5000 rpm, 2 minutes, −10° C. and 23° C. for the −16° C. and 25° C. samples, respectively). The lorazepam samples had completely dissolved at both temperatures, so the measured concentration indicates only a lower limit of solubility. Clonazepam was measured by UV at 350 nm; all others at 300 nm. The solubilities shown below in Table 7B indicate that solubility is sufficient over a wide range of temperature to achieve therapeutic dose of these benzodiazepines.

TABLE 7B

Solubility of Benzodiazepines in Transcutol ®

|  | T = 25° C. | T = −16° C. |
| --- | --- | --- |
| Clonazepam | 38.9 | 35.3 |
| Lorazepam | >110 | >130 |
| Diazepam | 96.5 | 87.6 |

Further, the solubility of clonazepam in binary mixtures of Transcutol® (TC), triacetin (TA), glycofurol (GF) and propylene glycol (PG) was evaluated. Solubility limits of clonazepam were determined for the following formulations:

TABLE 8

Binary Mixture Formulations

| Formulation | Composition |
| --- | --- |
| K | 70% GF + 30% TA |
| R | 30% GF + 60% PG + 10% citrate/TWEEN/metabisulfite |
| T | 30% GF + 70% PG |
| i | 30% GF + 70% TA |
| ii | 50% TC + 50% TA |
| iii | 50% TC + 50% PG |

Excess drug (50 mg) was capped with about 500 µL of the solvent matrix in a 1.5 mL microfuge tube and the solution was mixed on a vortex shaker for several minutes. Thereafter, the solution was placed in an ultrasonic bath at 25° C. for 45 minutes. The temperature was regulated with a thermometer and controlled by adding ice into the bath. After 15 minutes of standing, the solutions were centrifuged at 3,000×g for 30 minutes. Solutions were then stored for 16 hours at 25° C. in an ICH cabinet protected from light.

The solubility of clonazepam in neat solvents was as shown in Table 7A. From the data in Table 7A, the theoretical solubility of clonazepam in mixtures was calculated. The results of the solubility tests and the theoretical values were as shown in Table 9.

TABLE 9

Solubility of Clonazepam in binary mixtures of matrices

| Formulation | Measured Solubility (mg/mL) | Theoretical solubility (mg/mL) | Meas./Theor. (%) |
| --- | --- | --- | --- |
| K - 70% GF + 30% TA | 49.8 | 48.8 | 102.0 |
| R - 30% GF + 60% PG + 10% c/t/m (aq) | 11.5 | 22.2 | 51.9 |
| T - 30 GF + 70% PG | 16.7 | 22.6 | 74.0 |
| i - 30% GF + 70% TA | 22.9 | 24.2 | 94.4 |
| ii - 50% TC + 50% TA | 27.6 | 22.2 | 123.9 |
| iii - 50% TC + 50% PG | 21.7 | 21.0 | 103.0 |

Figure 2:
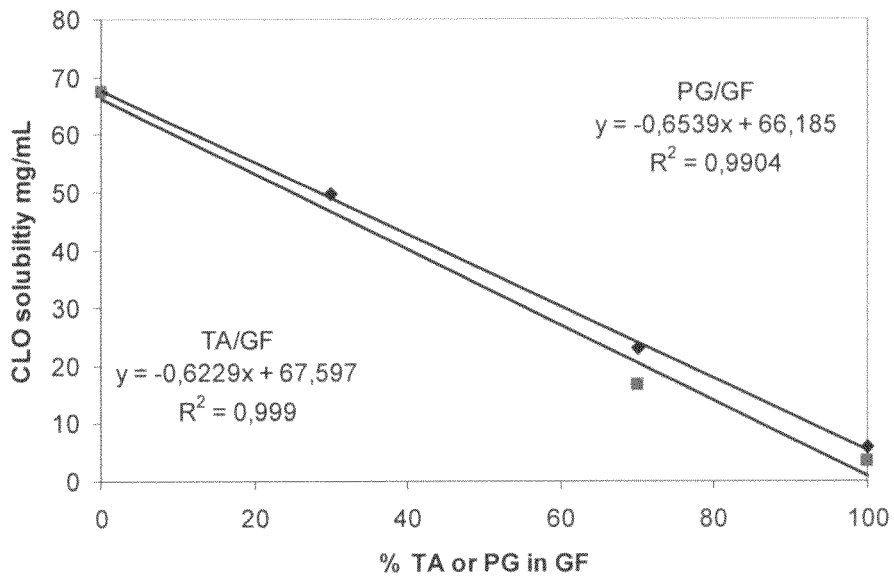
FIG. 2 presents the solubility of clonazepam in mixtures of triacetin or propylene glycol and glycofurol. In the figure, the vertical axis is CLO (clonazepam) solubility in mg/mL, and the horizontal axis is the percent (%) triacetin (TA) or propylene glycol (PG) and glycofurol (GF). In the figure, the linear regression for PG/GF was y=−0.6539x+66.185, with a correlation coefficient of $R^2$=0.9904; and the linear regression for TA/GF was y=−0.6229x+67.597, with a correlation coefficient of $R^2$=0.999.

Further, the data presented in FIG. 2 demonstrated a linear relationship between the solubility and composition (based on percents) of the binary mixtures of triacetin and glycofurol, as well as propylene glycol and glycofurol. From the data in the figure, it can be inferred that the solubility in the 50:50 mixture would be about 36.4 mg/mL. Based on the data the solubility of clonazepam in binary mixtures of GF and PG the relationship between solubility and composition does not appear to be as linear as it is in the mixtures of GF and TA.

These data demonstrate the usefulness of solvent solutions comprising binary solvent mixtures to solubilize clonazepam, for example, for use in formulation of intranasal pharmaceutical compositions.

The solvent systems set forth in Table 8 and Table 9 provide examples of formulations with a minimum number of solvent components in the system which helps reduce possible interactions. These solvent combinations also increase the chemical potential and system thermodynamics helping to ensure that the drug (e.g., clonazepam) prefers to cross the nasal membrane due to decreasing solubility. The solvent systems set forth in Table 8 and Table 9 also avoid components that may provide a thermodynamic sink (e.g., PEG and cyclodextrins) where clonazepam would prefer to remain in the nasal cavity with a non-penetrating excipient.

Example 3

Further Stability Studies

Eighteen 20 mg/mL clonazepam formulations were set up for accelerated stability studies: six weeks held at 60° C. with exposed head-space. Samples were withdrawn at 0, 1, 2, 4 and 6 weeks and assayed for clonazepam at 20,000 fold dilution and for degradation products at 20-fold dilution. Color was assessed by visual inspection at 6 weeks. Clonazepam is subject to both oxidative (color) and hydrolytic (chemical) degradation. Oxidative degradation was scored using a relative color scale of 1 (lightest=least degradation) to 5 (darkest=most degradation). Hydrolytic degradation was evaluated by sampling and analysis of the sample using HPLC and a clonazepam reference standard. The results of these analyses are presented in Table 10.

TABLE 10

Stability Screen at 60° C.

| # | Formulations | Chemical Degradation % Clonazepam remaining | | | | | Oxidative Color/ |
|---|---|---|---|---|---|---|---|
| | | 0 wks | 1 wk | 2 wks | 4 wks | 6 wks | 6 wks |
| 1 | 100% Glycofurol | 96% | 101% | 96% | 90% | 81% | 1 |
| 2 | 95% Glycofurol + 5% H$_2$O | 94% | 105% | 99% | 82% | 68% | 4 |
| 3 | 100% Transcutol ® | 100% | 111% | 103% | 94% | 88% | 1 |
| 4 | 90% Transcutol ® + 10% H$_2$O | 98% | 100% | 94% | 79% | 67% | 4 |
| 5 | 80% Glycofurol + 20% Transcutol ® | 84% | 99% | 99% | 93% | 82% | 2 |
| 6 | 70% Glycofurol + 20% Transcutol ® + 10% H$_2$O | 113% | 99% | 93% | 72% | 63% | 5 |
| 7 | 70% Glycofurol + 30% Triacetin | 104% | 108% | 105% | 91% | 82% | 2 |
| 8 | 30% GF + 70% PEG 200 | 105% | 93% | 79% | 67% | 60% | 4 |
| 9 | 50% Glycofurol + 50% Transcutol ® | 108% | 107% | 97% | 86% | 73% | 3 |
| 10 | 50% Transcutol ® + 50% PEG 200 | 96% | 93% | 79% | 76% | 68% | 4 |
| 11 | 70% Transcutol ® + 30% Triacetin | 106% | 110% | 101% | 99% | 92% | 1 |
| 12 | 60% Transcutol + 30% Triacetin + 10% H$_2$O | 104% | 108% | 101% | 86% | 78% | 3 |
| 13 | 60% Transcutol ® + 30% Triacetin + 10% 10 mM citrate pH 4 | 107% | 105% | 104% | 96% | 91% | 2 |
| 14 | 60% Transcutol ® + 30% Triacetin + 10% 10 mM phosphate pH 4 | 102% | 108% | 109% | 101% | 92% | 2 |
| 15 | 60% Transcutol ® + 40% Propylene glycol | 105% | 110% | 104% | 95% | 89% | 2 |
| 16 | 5% GF + 95% PEG200 | 106% | 89% | 74% | 61% | 53% | 5 |
| 17 | 10% GF + 90% PEG200 | 99% | 85% | 77% | 62% | 55% | 5 |
| 18 | 10% TC + 90% PEG200 | 102% | 88% | 77% | 64% | 54% | 5 |

After a 2-week incubation at 60° C. it was evident from the assay results that formulations containing PEG were the least stable formulations. These results were corroborated in the clonazepam assay (% clonazepam remaining) after four weeks and six weeks. After two weeks, the percent clonazepam had dropped below 80% in all formulations containing PEG and down to 50-60% in the formulations containing 70-95% PEG and 68% in the formulation containing 50% PEG.

Formulations containing 5-10% water also demonstrated some level of clonazepam instability. Thus, the percent clonazepam dropped to 63-78% in 6 weeks at 60° C. In contrast to the formulations containing 5-10% water the formulations containing 10% aqueous buffer at pH 4 demonstrated relatively high stability. Thus, the assay of those formulations was in the 90% range after 6 weeks of storage at 60° C.

Concomitant with the drop in percent clonazepam, an intense color development was seen in those formulations, as all PEG containing formulations scored 4 or 5 in color intensity at 6 weeks. Formulations that contained water without buffer also demonstrated color development and scored from 3 to 5 after 6 weeks of storage. This is clearly exemplified by formulation 1 and 2, 3 and 4, and 5 and 6. These observations suggested that the color development may be related to hydrolysis events.

Comparison of degradation product HPLC profile of the formulations containing water with forced degradation samples which were exposed to HCl, NaOH and H$_2$O$_2$ revealed that the similarity is greatest with the degradation products from incubation with HCl which further supports the theory of hydrolysis. In contrast, formulations with water that were buffered at pH 4 (#13 and 14) demonstrated only low color development and scored 2. This indicated that hydrolysis can be prevented by keeping the pH at a low level (for example, increased stability of benzodiazepines in the pH range 4.5 to 5.5, see, e.g., P.C.T. International Publication No. WO 91/16929; and Pharmazie, 1974 October-November, 29(10-11), pages 700-707).

As can be seen from the results presented in Table 10, better stability was generally achieved in the absence of free PEG polymers. The data presented above indicated that PEGs lead to an increase in degradation of clonazepam. Similarly, water appeared to contribute to increased degradation of clonazepam as well. In view of the results presented above, an anhydrous solvent matrix for clonazepam is preferred. Further, formulations without PEG also appeared to be preferred in order to improve clonazepam stability.

Addition of an anti-oxidant to the formulations of the present invention used for intranasal delivery of benzodiazepines may provide desirable protective benefits to such formulations. Examples of a suitable anti-oxidants include, but are not limited to, tocopherol and derivatives thereof, ascorbic acid and derivatives thereof, butylhydroxyanisole, butylhydroxytoluene, fumaric acid, malic acid, propyl gallate, sodium sulfite, metabisulfites (including sodium metabisulfite) and derivatives thereof, as well as EDTA disodium, trisodium and the tetrasodium salts. Soluble, organic anti-oxidants are preferred, for example, butylhydroxytoluene.

Further, the data indicate protective effects resulting from the inclusion of pH modifiers when an aqueous solvent was used. Microbial challenge with 5 organisms (*staphylococcus aureas, pseudomonas aeruginosa, escherichia coli, candida albicans* and *aspergillus niger*) showed a log plate count of less than 1/mL observed after a period of 28 days, indicating that the liquid formulation itself is microcidal and therefore a non-sterile product is likely acceptable.

Example 4

Screening Formulations for Nasal Irritation Potential Using a Rat Model

A number of formulations were tested in a rat irritation model. The first objective was to establish the irritation threshold of Transcutol®. Two formulations were tested containing 20% and 50% Transcutol® in PEG 200. The blood pressure signals integrated as a function of time were as shown in FIG. 3.

Figure 3:
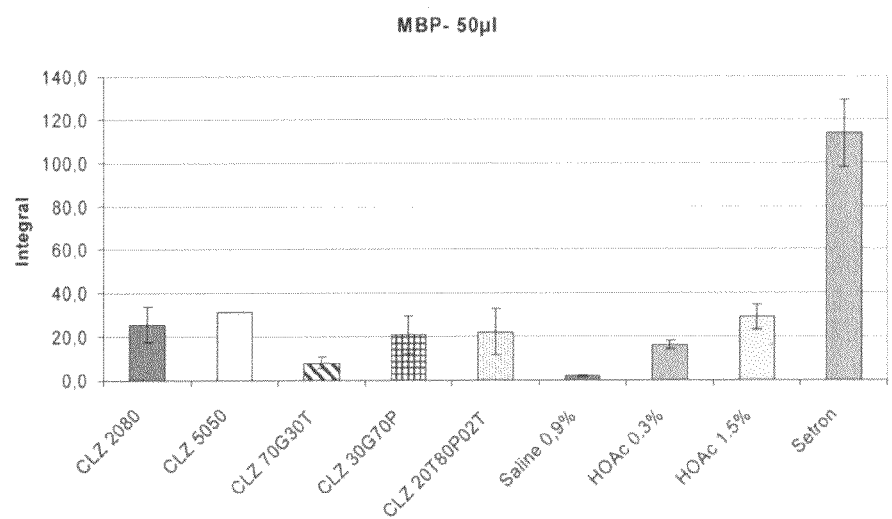
FIG. 3 presents irritation data for five clonazepam formulations. Comparison of irritation values is given relative to acetic acid solutions and a setron formulation. In the figure, the vertical axis is the blood pressure integrated as a function of time (Integral) and the horizontal axis is the formulations tested at 50 µL doses, as follows: CLZ2080—10 mg/mL clonazepam, 20% Transcutol® (TC), 80% Polyethylene Glycol (PEG); CLZ5050—10 mg/mL clonazepam, 50% TC, 50% PEG; CLZ70G30T—10 mg/mL clonazepam, 70% GF, 30% TA; CLZ20T80P02T, 10 mg/mL clonazepam, 10% TC, 90% PEG 200 and 0.2% Tween 20; Saline (negative control); Acetic Acid (HOAc) 0.3% (positive control); Acetic Acid (HOAc) 1.5% (positive control); Setron (positive control).

In FIG. 3, the designations were as follows: CLZ2080—10 mg/mL clonazepam, 20% Transcutol® (TC), 80% Polyethylene Glycol (PEG); CLZ5050—10 mg/mL clonazepam, 50% TC, 50% PEG; CLZ70G30T-10 mg/mL clonazepam, 70% GF, 30% TA; CLZ20T80P02T, 10 mg/mL clonazepam, 10% TC, 90% PEG 200 and 0.2% TWEEN 20; Saline (negative control); Acetic Acid (HOAc) 0.3% (positive irritation control); Acetic Acid (HOAc) 1.5% (positive irritation control); Setron (positive irritation control).

The data shown in FIG. 3 demonstrated slight, transient irritation apparent in the test animals. After instillation of compositions, irritation typically lasted less than 1.5 minutes in rats (range 0.7 to 2.2 minutes). Irritation was generally greater than saline and similar to irritation from 1.5% acetic acid. Veterinary evaluation of the data resulted in the conclusion that nasal irritation from these formulations was not significant.

Two other clonazepam formulations were tested (70% PEG and 30% GF; and 10% TC, 90% PEG 200 and 0.2% Tween 20) and similar results were obtained. Tween 20 (polyethylene glycol sorbitan monolaurate) was used as a possible irritation reducer.

One formulation, CLZ5050 appeared to produce more intense irritation than the other formulations as instillation was associated with a blood pressure drop. The drop biased the drawing of a base line and therefore the integration of the signal:

In a second rat nasal irritation experiment, eight clonazepam formulations and one formulation matrix without clonazepam (K: 30% TA, 70% GF) were tested in the irritation model and compared with irritation results obtained using 0.9% acetic acid. The formulations used in and results from the rat nasal irritation study are presented in Table 11. In the table, Iden. —is the identifier associated with the formulation; MBP—integrated mean blood pressure over the duration of the irritation response; T—duration of irritation response (minutes); TC—Transcutol®; PEG—polyethylene glyco; TA—triacetin; GF—glycofurol; PG—propylene glycol; H2O—water; Tw—TWEEN 20; w/o clz=without clonazepam. Fifty µL of each formulation containing 20 mg/mL clonazepam was administered to each animal.

Sodium metabisulfite and citric acid were each present at less than 1% (w/w) basis in the above formulations.

Figure 4:
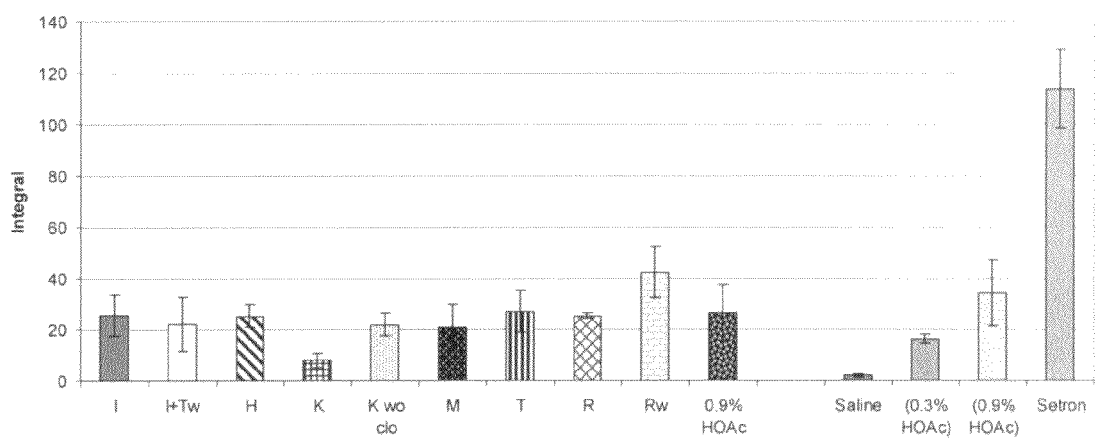
FIG. 4 presents that data for irritation scores of eight clonazepam formulations and control formulations based on the mean blood pressure changes. The columns for saline, acetic acid solutions and a setron formulation (i.e., the right-most four columns) represented data from previous experiments and were inserted for comparison. In the figure, the vertical axis is the blood pressure integrated as a function of time (Integral) and the horizontal axis corresponds to the tested formulations (the formulations are set forth in Table 11). Saline was a negative control; 0.3% Acetic Acid (HOAc) and 0.9% HOAc were positive irritation controls; and setron was a positive irritation control.

Acetic acid 0.9% has been found to be tolerated by volunteers in a human trial. The objective of this experiment was to provide a preliminary test a variety of formulations and compare them with respect to irritation. Because a slightly irritating profile would be tolerated for an intranasal formulation against seizure clusters and other acute indications such as panic attacks, the major concern was that volunteers participating in a clinical Phase I trial would not suffer unnecessary pain. The irritation scores based on measurement of blood pressure are presented in FIG. 4 and Table 11. In FIG. 4, the columns for saline, acetic acid solutions and a setron formulation (i.e., the right-most four columns) represented data from previous experiments and were inserted for comparison. Table 11 also present the duration of the irritation response in minutes. The results showed that all formulations tested gave a relatively short-lived irritation response, in the range from 0.7 to 2.2 minutes.

To test the irritation of Transcutol®, two formulations were tested containing 20% and 50% Transcutol® with PEG 200 as the cosolvent. Transcutol® at 20% (I) or 50% (H) demonstrated similar irritation scores suggesting that Transcutol® is no more irritating than PEG. A third formulation containing Transcutol® was the same as I but with 0.2% Tween. Comparison of I and I with Tween-20 suggested that Tween did not provide a substantial reduction of irritation in this formulation.

Formulation K (30% TA, 70% GF), which showed a good pharmacokinetic profile (see Example 5), had the lowest irritation score of the formulations tested in this experiment.

Formulation K was also tested without clonazepam to obtain information on the effects of clonazepam on irritation. Comparison of the irritation scores of K and K without clonazepam showed that clonazepam appeared to have an irritation reducing effect.

Formulations M and T contain the same amount of glycofurol but M contains 70% PEG while T contains propylene glycol as the cosolvent. The irritation score of these two does not differ significantly indicating a similar degree of irritation by PG and PEG.

TABLE 11

Rat Nasal Irritation Study

| | Formulation | | | | | | | | MBP | | T (min) | |
|---|---|---|---|---|---|---|---|---|---|---|---|---|
| Iden. | TC | PEG | TA | GF | PG | H2O | Tw | N | aver. | stdev[c] | Avg | err[c] |
| I | 20 | 80 | | | | | | 3 | 26 | 8 | 1.8 | 0.2 |
| H | 50 | 50 | | | | | | 4[a] | 25 | 4 | 1.9 | 0.2 |
| K | | | 30 | 70 | | | | 3 | 8 | 3 | 0.7 | 0.1 |
| M | | 70 | 30 | | | | | 3 | 21 | 9 | 1.7 | 0.1 |
| I + Tw | 20 | 80 | | | | | 0.2 | 3 | 22 | 11 | 1.2 | 0.2 |
| T | | | 30 | 70 | | | | 2[b] | 27 | (8) | 1.2 | (0.1) |
| R_wa | | | 30 | 60 | 10 | | | 3 | 42 | 10 | 1.8 | 0.5 |
| R | | | 30 | 60 | 10[d] | | 0.2 | 3 | 25 | 1 | 2.2 | 0.2 |
| K w/o clz | | | 30 | 70 | | | | 3 | 22 | 4 | 1.3 | 0.2 |
| 0.9% HOAc | | | | | | | | 2 | 26 | 11 | 1.6 | (0.3) |

[a] = blood pressure drop must be due to intense irritation. The drop biases the drawing of a base line and therefore the integration of the signal.
[b] = the third animal in the group reacted very strongly to administration, received cardiac resuscitation. The results from this animal were not included in the data processing.
[c] = numbers in parentheses are used when n < 3.
[d] = includes citrate buffer pH4, and sodium metabisulphite.

Formulation R with 10% buffer (citrate/Tween/bisulphite) or with 10% water was the only water containing formulation tested. The formulation with water only appeared to be significantly more irritating than the formulation that contained buffer/Tween/bisulphite. Formulation R with buffer demonstrated similar irritation profile as did the non-aqueous formulations I, H, M and T.

Acetic acid 0.9% has been tested for irritation in a human trial and was found to be irritating but tolerable. All formulations tested except R with water demonstrate irritation equal or lower than this reference formulation (FIG. 4) suggesting that they had minor irritation but were tolerable.

These nasal irritation data suggested that the clonazepam formulations of the present invention were suitable for intranasal delivery.

Example 5

Pharmacokinetics and Tolerability

Different clonazepam formulations were delivered intranasally and intravenously to rabbits. Many of the administrated formulations demonstrated intranasal bioavailability higher than 70% that of the intravenous formulations. Those that contained Transcutol® at concentrations 20-100% demonstrating that Transcutol® was a useful absorption enhancer and solvent for clonazepam Additionally, the intranasal clonazepam formulations containing Transcutol® in the concentration range 20-100% yielded pharmacokinetic (PK) profiles with $t_{max}$ lower than 4 minutes. The absorption enhancing effects of Transcutol®V were also demonstrated by this performance index.

Some exemplary pharmacokinetic data for clonazepam formulations is presented in Table 12A (N=1 for each formulation). In the table, Tw or tween is TWEEN20, EtOH is ethanol, Triac or TA is Triacetin, phosph is phosphate buffer, metabisulph is sodium metabisulphite, citr is citrate buffer, AUC is area under the curve $T_{max}$ is minutes, $C_{max}$ is in ng/ml, and F % is bioavailability of the intranasal formulation as compared to the intravenous formulation—other abbreviations are as used herein above.

TABLE 12A

Example Clonazepam Formulations and Pharmacokinetic Data

| Formulation | PEG | TA | TC | GF | PG | Tw | EtOH | H2O | Dose (mg) | $T_{max}$ | $C_{max}$ | AUC | F % |
|---|---|---|---|---|---|---|---|---|---|---|---|---|---|
| 100% Transcutol ® | | | 100 | | | | | | 0.191 | 1.4 | 26 | 1048 | 125% |
| 30% Triacetin + 70% Transcutol ® | | 30 | 70 | | | | | | 0.201 | 1.1 | 50 | 1039 | 118% |
| 30% Triac. + 60% TC + 10% H2O | | 30 | 60 | | | | | 10 | 0.190 | 1.1 | 29 | 1165 | 111% |
| 40% PG + 60% TC | | | 60 | | 40 | | | | 0.195 | 2.9 | 45 | 1182 | 110% |
| 30% TA + 60% TC + 10% citrate | | 30 | 60 | | | | | 10 | 0.187 | 1.9 | 31 | 1130 | 110% |
| 30% Triacetin + 70% Transcutol ® | | 30 | 70 | | | | | | 0.201 | 3.0 | 39 | 902 | 102% |
| 90% TC + 10% H2O | | | 90 | | | | | 10 | 0.192 | 3.0 | 39 | 1157 | 109% |
| 30% TA + 60% TC + 10% citrate | | 30 | 60 | | | | | 10 | 0.187 | 3.0 | 26 | 938 | 91% |
| 30% TA + 60% TC + 0.2% tween + 10% citrate pH 4 | | 30 | 60 | | | | | 10 | 0.191 | 1.4 | 23 | 758 | 91% |
| 100% Transcutol ® | | | 100 | | | | | | 0.191 | 1.6 | 39 | 789 | 94% |
| 80% GF + 20% TC | | | 20 | 80 | | | | | 0.212 | 2.7 | 29 | 963 | 83% |
| 80% GF + 20% TC | | | 20 | 80 | | | | | 0.212 | 3.3 | 34 | 980 | 84% |
| 30% Triac. + 60% TC + 10% H2O | | 30 | 60 | | | | | 10 | 0.190 | 1.5 | 24 | 978 | 94% |
| 50% PEG200 + 50% TC | 50 | | 50 | | | | | | 0.196 | 1.6 | 44 | 1105 | 102% |
| 40% PG + 60% TC | | | 60 | | 40 | | | | 0.195 | 3.3 | 24 | 1021 | 95% |
| 30% TA + 60% TC + 10% phosph. | | 30 | 60 | | | | | 10 | 0.187 | 1.8 | 18 | 826 | 80% |
| 100% Glycofurol | | | | 100 | | | | | 0.191 | 15.6 | 18 | 876 | 105% |
| 50% GF + 50% TC | | | 50 | 50 | | | | | 0.218 | 2.2 | 38 | 1185 | 99% |
| 30% TA + 70% GF | | 30 | | 70 | | | | | 0.191 | 3.4 | 20 | 811 | 77% |
| 90% TC + 10% H2O | | | 90 | | | | | 10 | 0.192 | 1.5 | 21 | 826 | 78% |
| 95% GF + 5% Tween-20 | | | | 95 | | 5 | | | 0.190 | 1.4 | 26 | 759 | 73% |
| 30% TA + 60% TC + 10% phosph. | | 30 | 60 | | | | | 10 | 0.187 | 1.4 | 23 | 679 | 66% |
| 50% PEG200 + 50% TC | 50 | | 50 | | | | | | 0.196 | 3.4 | 30 | 839 | 78% |
| 10% GF + 0.2% tween + 90% PEG 200 | 90 | | | 10 | | | | | 0.182 | 5.7 | 13 | 642 | 81% |
| 100% GF | | | | 100 | | | | | 0.212 | 3.1 | 18 | 682 | 58% |
| 100% GF | | | | 100 | | | | | 0.212 | 1.6 | 20 | 647 | 55% |
| 30% TA + 70% GF | | 30 | | 70 | | | | | 0.191 | 5.4 | 15 | 707 | 67% |
| 10% GF + 0.2% tween + 90% PEG 200 | 90 | | | 10 | | | | | 0.182 | 3.7 | 10 | 414 | 52% |
| 10% TC + 0.2% tween + 90% PEG 200 | 90 | | 10 | | | | | | 0.193 | 9.9 | 18 | 650 | 77% |
| 50% PG + 20% TC + 20% EtOH + 10% citr/Tween/metabisulph | | | 20 | | 50 | | 20 | 10 | 0.200 | 15.6 | 33 | 1332 | 84% |
| 50% PG + 20% TC + 20% EtOH + 10% citr/Tween/metabisulph | | | 20 | | 50 | | 20 | 10 | 0.200 | 1.3 | 52 | 1133 | 72% |
| 30% GF + 60% PEG200 + 10% citr/Tween/metabisulph | 60 | | | 30 | | | | 10 | 0.200 | 3.0 | 16 | 728 | 46% |
| 30% GF + 60% PEG200 + 10% citr/Tween/metabisulph | 60 | | | 30 | | | | 10 | 0.200 | 3.5 | 42 | 773 | 49% |
| 100% PEG 300 | 100 | | | | | | | | 0.201 | 20.9 | 17 | 690 | 79% |
| 100% PEG 200 | 100 | | | | | | | | 0.195 | 3.3 | 15 | 475 | 56% |
| 10% GF + 90% PEG 200 | 90 | | | 10 | | | | | 0.211 | 3.0 | 13 | 589 | 64% |

TABLE 12A-continued

Example Clonazepam Formulations and Pharmacokinetic Data

| Formulation | PEG | TA | TC | GF | PG | Tw | EtOH | H2O | Dose (mg) | $T_{max}$ | $C_{max}$ | AUC | F % |
|---|---|---|---|---|---|---|---|---|---|---|---|---|---|
| 10% GF + 90% PEG 200 | 90 | | | 10 | | | | | 0.211 | 5.6 | 16 | 678 | 73% |
| 30% TA + 60% TC + 0.2% tween + 10% citrate pH 4 | | 30 | 60 | | | | | 10 | 0.191 | 1.4 | 23 | 482 | 58% |
| 10% TC + 0.2% tween + 90% PEG 200 | 90 | | 10 | | | | | | 0.193 | 46.4 | 13 | 640 | 76% |
| 80% PEG200 + 20% TC | 80 | | 20 | | | | | | 0.198 | 3.0 | 17 | 750 | 69% |
| 10% GF + 80% PEG + 10% citr/Tween/metabisulph | 80 | | | 10 | | | | 10 | 0.200 | 3.8 | 25 | 840 | 53% |
| 30% GF + 70% PG | | | | 30 | 70 | | | | 0.200 | 4.7 | 28 | 956 | 60% |
| 5% GF + 95% PEG 200 | 95 | | | 5 | | | | | 0.200 | 15.1 | 14 | 622 | 71% |
| 50% GF + 50% TC | | | 50 | 50 | | | | | 0.218 | 3.0 | 10 | 298 | 25% |
| 70% GF + 20% TC + 10% H2O | | | 20 | 70 | | | | 10 | 0.214 | 5.3 | 20 | 655 | 56% |
| 30% GF + 70% PEG200 | 70 | | | 30 | | | | | 0.189 | 5.8 | 9 | 445 | 43% |
| 30% GF + 70% PEG200 | 70 | | | 30 | | | | | 0.189 | 15.0 | 14 | 653 | 63% |
| 10% GF + 50% PEG + 30% PG + 10% citr/Tween/metabisulph | 50 | | | 10 | 30 | | | 10 | 0.200 | 3.4 | 25 | 748 | 47% |
| 30% GF + 70% PG | | | | 30 | 70 | | | | 0.200 | 2.9 | 14 | 585 | 37% |
| 30% GF + 70% PG | | | | 30 | 70 | | | | 0.200 | 3.4 | 15 | 332 | 21% |
| 10% GF + 80% PEG + 10% citr/Tween/metabisulph | 80 | | | 10 | | | | 10 | 0.200 | 3.1 | 23 | 459 | 29% |
| 10% GF + 50% PEG + 30% PG + 10% citr/Tween/metabisulph | 50 | | | 10 | 30 | | | 10 | 0.200 | 3.3 | 17 | 288 | 37% |
| 100% PEG 200 | 100 | | | | | | | | 0.195 | 21.3 | 9 | 400 | 47% |
| 80% PEG200 + 20% TC | 80 | | 20 | | | | | | 0.198 | 10.4 | 12 | 593 | 54% |
| 100% PEG 300 | 100 | | | | | | | | 0.201 | 30.4 | 9 | 427 | 49% |
| 5% GF + 95% PEG 200 | 95 | | | 5 | | | | | 0.200 | 5.4 | 10 | 297 | 34% |
| 95% GF + 5% Tween-20 | | | | 95 | | 5 | | | 0.190 | 44.8 | 10 | 518 | 50% |
| 10% GF + 80% PEG + 10% citr/Tween/metabisulph | 80 | | | 10 | | | | 10 | 0.200 | 30.4 | 14 | 636 | 40% |
| 70% GF + 20% TC + 10% H2O | | | 20 | 70 | | | | 10 | 0.214 | 60.0 | 6 | 270 | 23% |

Sodium metabisulfite and citric acid were each present at less than 1% (w/w) basis in the above formulations.

Some clonazepam formulations without Transcutol® also provided a rapid rise in blood levels post-intranasal dosing including, for example, 95% GF, 5% Tween-20, 100% GF, 10% GF, 90% PEG, 100% PEG and 30% TA, 70% GF.

The pharmacokinetic data presented above illustrated that clonazepam compositions formulated for intranasal administration are pharmaceutically efficacious to deliver clinically relevant amounts of clonazepam into the bloodstream in a short time period—making such intranasal formulations clinically useful, for example, for the treatment of seizure clusters. Such clonazepam compositions comprise, for example, one or more solvents selected from the group including, but not limited to, Transcutol® (diethylene glycol monoethylether) and similar alkylethers, propylene glycol, triacetin, Glycofurol (ethoxylated furanyl alcohol or tetrahydrofurfuryl alcohol polyethyleneglycol ether) and similar ethoxylated tetrahydrofurfuryl alcohols, as well as polyethylene glycol (e.g., PEG 200, PEG 300, etc.). However, as noted above, free PEG polymers lead to reduced stability of clonazepam formulations.

The data shown in Table 12 above were reanalyzed. The rabbit pilot PK experiments had been performed in two groups of ten animals, JC01 (Group 1) and JC02 (Group 2). The JC01 experiments were performed in a group of rabbits which were older and heavier than the JC02 group of rabbits. Each group of rabbits had their own set of intravenous clonazepam PK data for the calculations of bioavailability.

The intranasal formulations were 4 mg/mL. The animals were administered 25 µL of formulation to each nostril, 50 µL in all, with an Eppendorf dosing pipette. The animal was held in a supine position while being dosed and for about 10 seconds after. The intravenous formulation, Rivotril® injectable, was administered as 500 µL injected over 30 seconds into the marginal ear vein on opposite site to the blood sampling ear. All rabbits received 0.2 mg clonazepam.

Five formulations were tested on each study day, where each of the formulations was administered to two rabbits. The data were analyzed before the composition of the formulations administered to the next group of animals was decided.

Due to the different body weights of the two rabbit groups, the $C_{max}$ and the 60 minute AUC results from the two groups were not directly comparable. The relative bioavailability was corrected for weight differences between the two groups, based on results of the IV administrations to each group. The $C_{max}$ was not directly comparable between the two groups, but was included in the table as a relative indication peak levels within each group.

TABLE 12B

Example Clonazepam Formulations and Pharmacokinetic Data

| ID | Formulation | Rabbit no. | Dose (mg) | t-max | C-max | Relative BA |
|---|---|---|---|---|---|---|
| | | Group 1 Rabbits | | | | |
| IV | Intravenous | 21-25 | 0.214 | | | 100% |
| 1 | 100% PEG 300 | 21 | 0.201 | 20.9 | 27.3 | 62% |
| | | 26 | 0.201 | 30.4 | 14.5 | 38% |
| 2 | 100% PEG 200 | 22 | 0.195 | 3.3 | 26.0 | 44% |
| | | 27 | 0.195 | 21.3 | 14.6 | 37% |
| 3 | 100% Glycofurol | 23 | 0.191 | — | — | — |
| | | 28 | 0.191 | 15.6 | 30.4 | 83% |
| 4 | 100% Transcutol | 24 | 0.191 | 1.4 | 44.6 | 99% |
| | | 29 | 0.191 | 1.6 | 64.9 | 74% |
| 5 | 30% Triacetin + 70% Transcutol | 25 | 0.201 | 3.0 | 64.6 | 81% |
| | | 30 | 0.201 | 1.1 | 81.5 | 93% |
| 6 | 10% GF + 90% PEG 200 | 21 | 0.211 | 5.6 | 27.4 | 61% |
| | | 26 | 0.211 | 3.0 | 25.8 | 58% |
| 7 | 5% GF + 95% PEG 200 | 22 | 0.200 | 5.4 | 20.2 | 32% |
| | | 27 | 0.200 | 15.1 | 27.1 | 65% |
| 8 | 10% GF + 0.2% tween + 90% PEG 200 | 23 | 0.182 | 3.7 | 23.9 | 59% |
| | | 28 | 0.182 | 5.7 | 20.1 | 55% |
| 9 | 30% TA + 60% TC + 0.2% tween + 10% citrate pH 4 | 24 | 0.191 | 3.0 | 48.5 | 90% |
| | | 29 | 0.191 | 1.4 | 43.5 | 53% |
| 10 | 10% TC + 0.2% tween + 90% PEG 200 | 25 | 0.193 | 46.4 | 24.0 | 67% |
| | | 30 | 0.193 | 9.9 | 32.8 | 66% |
| | | Group 2 Rabbits | | | | |
| A | IV | 33 + 35 | 0.214 | | | 100% |
| B | 100% GF | 31 | 0.212 | 3.1 | 19.9 | 53% |
| | | 32 | 0.212 | 1.6 | 23.2 | 54% |
| C | 80% GF + 20% TC | 34 | 0.212 | 2.7 | 31.2 | 73% |
| | | 36 | 0.212 | 3.3 | 39.7 | 78% |
| D | 50% GF + 50% TC | 37 | 0.218 | 2.2 | 41.1 | 79% |
| | | 38 | 0.218 | 3.0 | 14.4 | 25% |
| E | 70% GF + 20% TC + 10% H2O | 39 | 0.214 | 5.3 | 25.2 | 51% |
| | | 40 | 0.214 | 3.2 | 9.5 | 20% |
| F | 90% TC + 10% H2O | 31 | 0.192 | 3.0 | 43.5 | 105% |
| | | 32 | 0.192 | 1.5 | 24.6 | 76% |
| G | 30% Triac. + 60% TC + 10% H2O | 33 | 0.190 | 1.5 | 30.5 | 84% |
| | | 34 | 0.190 | 1.1 | 31.1 | 103% |
| H | 50% PEG200 + 50% TC | 35 | 0.196 | 1.6 | 47.2 | 94% |
| | | 36 | 0.196 | 3.4 | 34.6 | 78% |
| I | 80% PEG200 + 20% TC | 37 | 0.198 | 3.0 | 17.9 | 59% |
| | | 38 | 0.198 | 10.4 | 14.1 | 53% |
| J | 95% GF + 5% Tween-20 | 39 | 0.190 | 44.8 | 10.9 | 47% |
| | | 40 | 0.190 | 1.4 | 29.6 | 73% |
| K | 30% Triacetin + 70% Glycofurol | 31 | 0.191 | 5.4 | 17.0 | 69% |
| | | 36 | 0.191 | 3.4 | 24.9 | 84% |
| L | 40% PG + 60% TC | 32 | 0.195 | 2.9 | 51.3 | 111% |
| | | 37 | 0.195 | 3.3 | 24.2 | 85% |
| M | 30% GF + 70% PEG200 | 33 | 0.189 | 15.0 | 17.3 | 69% |
| | | 38 | 0.189 | 5.8 | 12.0 | 48% |
| N | 30% TA + 60% TC + 10% citrate | 34 | 0.187 | 1.9 | 33.7 | 105% |
| | | 39 | 0.187 | 3.0 | 30.9 | 94% |
| O | 30% TA + 60% TC + 10% phosph. | 35 | 0.187 | 1.8 | 19.8 | 76% |
| | | 40 | 0.187 | 1.4 | 27.9 | 72% |
| P | 10% GF + 80% PEG200 + 10% citr/tween/metab | 36 | 0.200 | 3.8 | 25 | 25% |
| | | 32 | 0.200 | 3.1 | 23 | 37% |
| | | 31 | 0.200 | 30.4 | 14 | 49% |
| Q | 10% GF + 50% PEG200 + 30% PG + 10% citr/tween/metab | 37 | 0.200 | 3.4 | 25 | 39% |
| | | 33 | 0.200 | 3.3 | 17 | 39% |
| R | 30% GF + 60% PG + 10% citr/tween/metab | 34 | 0.200 | 3.0 | 16 | 51% |
| | | 38 | 0.200 | 3.5 | 42 | 43% |
| T | 30% GF + 70% PG | 35 | 0.200 | 4.7 | 28 | 49% |
| | | 39 | 0.200 | 2.9 | 14 | 35% |
| | | 40 | 0.200 | 3.4 | 15 | 22% |
| U | 50% PG + 20% EtOH + 20% TC + 10% citr/tween/metab | 32 | 0.200 | 15.6 | 33 | 69% |
| | | | 0.200 | 1.3 | 52 | 72% |

Note:
Tw or tween is TWEEN20,
EtOH is ethanol,
Triac or TA is Triacetin,
phosph is phosphate buffer,
metabisulph is sodium metabisulphite,
citr is citrate buffer.

As exemplified in Tables 12A and 12B above, the composition may comprise a solvent matrix of two solvents, for example, a first solvent that provides high solublization of clonazepam (for example, TC or GF) that, after application to nasal mucosa, is absorbed by the nasal mucosa leading to clonazepam super saturation, and a second solvent (for example, TA or PG) in which clonazepam has lower solubility relative to the first-solvent. In preferred embodiments, the compositions are substantially non-aqueous or anhydrous; however, the compositions may further comprise an aqueous component (for example, of less than about 10% aqueous content, preferably of less than about 5% aqueous content, more preferably of less than about 2% aqueous content, wherein the aqueous content is preferably buffered with a physiologically acceptable buffer to obtain a pH range of about pH 4 to about pH 7, preferably between about pH 4 to about pH 6.5). The benzodiazepine compositions of the present invention may comprise further components as well, for example, anti-oxidants (for example, sodium metabisulfite or butylhydroxytoluene (BHT). Preferred embodiments typically do not include polyethylene glycol polymers as a solvent but may include solvents like tetrahydrofurfuryl alcohol polyethyleneglycol ether (Glycofurol) wherein the solvent molecules contain polyethylene glycol polymers as an intrinsic part of their molecular structure, that is, polyethylene glycol polymers as substituent groups of a larger chemical structure (also, see, for example, published P.C.T. International Patent Application Nos. WO 03/070273 and WO 03/070280).

The pharmacokinetics and tolerability of four clonazepam compositions comprising binary solvent systems were further evaluated. The four formulations were as follows in Table 13.

TABLE 13

Compositions of binary solvent systems (10 mg/mL clonazepam)

| Composition | Solvent System |
|---|---|
| I | 50% diethyleneglycol monoethylether + 50% triacetin |
| II | 50% diethyleneglycol monoethylether + 50% propylene glycol |
| III | 50% glycofurol + 50% triacetin |
| IV | 50% glycofurol + 50% propylene glycol |

The pharmacokinetics of the formulations in Table 13 were evaluated by nasal administration to rabbits and compared to intravenous (i.v.) administration of clonazepam in rabbits. Sample size for each formulation was N=10 with instillation of 10 mg/mL clonazepam dose adjusted to body weight. A summary of the data is presented in FIG. 5.

The data is further summarized in Table 14.

TABLE 14

PK Data for Selected Formulations

| Formulation | Dose (mg) | $T_{max}$ | $C_{max}$ | AUC | Bioavail. |
|---|---|---|---|---|---|
| I | 50% TC + 50% TA | 0.214 | 20.3 | 9.02 | 462 | 43% |
| II | 50% TC + 50% PG | 0.214 | 3.51 | 24.31 | 704 | 66% |
| III | 50% GF + 50% TA | 0.214 | 3.24 | 10.14 | 454 | 43% |
| IV | 50% GF + 50% PG | 0.214 | 3.26 | 19.34 | 604 | 57% |
| Intravenous | Injected Rivotril | 0.214 | 1.70 | 49.70 | 1061 | 100% |

The intranasal PK profiles of the formulations presented above demonstrated a rapid absorption of clonazepam such that clinically relevant amounts of clonazepam reach the bloodstream in a short period of time. Short-term bioavailability does not necessarily need to be high; it is of higher importance that the blood levels become high in as short a time as possible. Lower bioavailability can be balanced out, for example, with higher dose. An advantage of a higher dose and low short term bioavailability may be passage of the drug that is not absorbed intranasally into the gastro-intestinal tract resulting in the remainder of the drug undergoing classical GI absorption leading to a sustained release profile.

As can be seen from the PK data in rabbits, benzodiazepine compositions of the present invention formulated for intranasal delivery may be characterized, for example, by a $T_{max}$ of benzodiazepine, after a single intranasal administration (in one or both nostrils), of 2 hours, often less than 1 hour likely less than 30 minutes or less than 15 minutes. Further, pharmaceutical compositions of benzodiazepines for intranasal delivery, as described herein, may be characterized, for example, by providing at least one of a mean maximum plasma concentration ($C_{max}$) of benzodiazepine of at least about 3.0 ng/mL or at least about 15% of the concentration of an intravenously delivered dose often 30% of an intravenously delivered dose or 50% or an intravenously delivered dose, and a mean plasma Area Under the Curve over 60 minutes (AUC) value of clonazepam of at least about 400 ng-hr/mL, when a single dose of the composition is administered intranasally to deliver a dose of at least about 0.2 mg of clonazepam. Further, the bioavailability of benzodiazepine compositions of the present invention, after intranasal administration, is typically greater than 30% often greater than 40% and frequently greater than 50% of that of intravenous administration.

In addition to the PK parameters discussed above, the experiments performed in support of the present invention evaluated the local tolerance in the upper and lower respiratory tract of formulations I-IV containing clonazepam as active drug. This tolerance was assessed in the rabbit as model. Treatments were performed during seven consecutive days before histopathological evaluation of selected tissues.

The rabbits used in these experiments were as follows: Breed, New Zealand White; Sek, 30 males and 30 females; Weight, Mean body weight 2.466±0.093 (SD) kg for the male rabbits, 2.465±0.114 (SD) kg for the female rabbits. Animals showing any concurrent disease at the time of the treatment were not included. Rabbits were obtained from Charles River Laboratories, L'Arbresle Cedex, France.

Animals were weighed during the acclimatisation period for allocation, within the 3 days prior to treatment and just before slaughter. The dose-level of 10 mg/mL (1 mg clonazepam in 100 µL solution) was selected to be comparable to an anticipated dose to be administered in humans.

The treatment groups are detailed in Table 15. Formulation 5 is a vehicle control—50% glycofurol; 50% propylene glycol (with no clonazepam). Formulation 6 is a saline control (0.9% NaCl in water).

TABLE 15

Allocation of treatments into groups

| Group | Treatment | Number of animals | Concentration of Clonazepam (mg/mL) | Number of treatments |
|---|---|---|---|---|
| 1 | Formulation I TC/TA+ | 5 males 5 females | 10 | 7 |
| 2 | Formulation II TC/PG+ | 5 males 5 females | 10 | 7 |

TABLE 15-continued

Allocation of treatments into groups

| Group | Treatment | Number of animals | Concentration of Clonazepam (mg/mL) | Number of treatments |
|---|---|---|---|---|
| 3 | Formulation III GF/TA+ | 5 males 5 females | 10 | 7 |
| 4 | Formulation IV GF/PG+ | 5 males 5 females | 10 | 7 |
| 5 | Formulation 5 GF/PG− | 5 males 5 females | 0 | 7 |
| 6 | Formulation 6 S− | 5 males 5 females | 0 | 7 |

The selected route of administration was the route of administration of the final product.

Whatever the formulation, 0.1 mL of the formulation was daily administered to all animals by nasal instillation during seven consecutive days.

All administrations were performed in the right nostril using a 1 mL pipette (B13, Adjustable pipettes Pipetman P200 from Gilson) fitted with a plastic cone. The required volume of item was measured with the pipette and placed just inside the nostril of the animal.

Treatment details were recorded in the raw data including dose administered, formulation identification, date and time of administration.

Six animals per group, three males and three females at Day 8, and the remaining animals at Day 15, after a seven-day recovery period, were sacrificed by ex-sanguination from abdominal aorta under isoflurane anaesthesia.

Following euthanasia, macroscopical examination of larynx, trachea, bronchi, lungs and oesophagus were performed.

The head of the animal, with the larynx and specimens of trachea, bronchi, lungs and oesophagus were taken at necropsy and fixed in formalin for histopathology.

From head, nasal mucosa, turbinates, in addition to larynx and trachea were sampled after specific preparation and examined. Any observed macroscopic abnormalities or lesions were also sampled and fixed, with a border of surrounding tissue, for histopathology.

Nasal mucosa and turbinates were examined in the nasal cavities on three head sections corresponding to nasal cavities proximal, nasal cavities turbinates and nasal cavities olfactory.

Histopathological examinations were performed and the results evaluated by a pathologist. All results were tabulated per group, means and standard deviations were calculated on each organ. Statistical comparisons were performed between group using ANOVA. There were no obvious differences in growth between groups.

Severity of the eventual modifications observed in the histological preparations were scored by the pathologist as follows: 0, no lesions; 1, slight; 2, moderate; and 3, severe.

FIG. 6 summarizes the histopathology results for the nasal cavities of the animals. Severity scores in group 3 was statistically higher than scores of groups 4, 5 and 6 (p=0.003). Irritative modifications like erosion and fibrino-leucocytic material in turbinates lumen were observed mainly in group 3 (⅔ females and ⅓ males), also for group 1 (⅓ females) and group 5 (⅔ males) but not for other treated or control groups. These modifications were not observed in necropsy on day 15. Mild epithelial atrophy on turbinates was noted in necropsy on day 8 and also in necropsy on day 15 mainly for treated group 1 and slighter for other treated groups. Control group 6 showed no epithelial atrophy. Blood was sometimes observed in aerian lumen for larynx and also nasal cavities both in treated and control groups and are probably of traumatic origin. The best local tolerance was observed for treated group 2 and 4. These results indicate generally good nasal tolerance for the tested formulations.

Blood or petechia were found in larynx on 15 animals (2 from group 1, 4 from group 2, 3 from group 3, 2 from group 4, 4 from group 5) during necropsy and on 6 animals (1 from group 2, 2 from group 4, 3 from group 5) at histopathology examination. Table 16 presents mean and SD severity scores in each group.

TABLE 16

Mean and SD severity score on larynx in each group

| | Group 1 | Group 2 | Group 3 | Group 4 | Group 5 | Group 6 |
|---|---|---|---|---|---|---|
| Mean score | 0.0 | 0.1 | 0.0 | 0.2 | 0.3 | 0.0 |
| SD | 0.0 | 0.3 | 0.0 | 0.4 | 0.5 | 0.0 |

Slight epithelial desquamation were observed on oesophagus from two animals from group 4. Table 17 presents mean and SD severity scores in each group.

TABLE 17

Mean and SD severity score on oesophagus in each group

| | Group 1 | Group 2 | Group 3 | Group 4 | Group 5 | Group 6 |
|---|---|---|---|---|---|---|
| Mean score | 0.0 | 0.0 | 0.0 | 0.2 | 0.0 | 0.0 |
| SD | 0.0 | 0.0 | 0.0 | 0.4 | 0.0 | 0.0 |

Petechia or blood were observed during necropsy on 17 animals (4 from group 1, 3 from group 2, 5 from group 3, 1 from group 4, 4 from group 5). No histopathological lesions were observed in bronchi and trachea.

Lung modifications were observed during necropsy on 17 animals (1 from group 1, 3 from group 2, 3 from group 3, 1 from group 6). Congestive foci were histologically recorded on two animals from group 2 at Day 15. Table 18 presents mean and SD severity scores in each group.

TABLE 18

Mean and SD severity score on lungs in each group

| | Group 1 | Group 2 | Group 3 | Group 4 | Group 5 | Group 6 |
|---|---|---|---|---|---|---|
| Mean score | 0.0 | 0.2 | 0.0 | 0.0 | 0.0 | 0.0 |
| SD | 0.0 | 0.4 | 0.0 | 0.0 | 0.0 | 0.0 |

Considering the whole respiratory tract, microscopical lesions were mainly observed in the very upper part, the nasal cavities. As no lesions were recorded in the control group, it is likely that all the lesions were related to the treatments. Petechia recorded at necropsy and presence of blood observed during histopathological examination can be due to a trauma induced by the treatment. In the majority of animals (20 out of the 26 presenting petechia or blood at necropsy), lesions recorded at necropsy were associated with histopathological findings. Irritative lesions were observed just after treatment and were not present after a one week recovery. Mild epithelial atrophy was observed after a one week recovery. Considering severity scores, formulation 3 induced significantly the most severe lesions. Local tolerances of the other formulation were nearly similar.

In conclusion, the results of necropsy and histopathological examination, including comparison of severity scores, suggested that the clonazepam compositions of the present invention comprising formulations for intranasal delivery have acceptable tolerability for pharmaceutical use.

Example 6

Sprayability and Viscosity of Solvent Matrices

Fourteen representative solvent matrices used for clonazepam formulations were tested for spray pattern and compared with water. The solvent mixtures were made up, spiked with minute amounts of Coomassie Brilliant Blue Dye and 100 μL were subsequently filled into Pfeiffer unit-dose devices (Pfeiffer of America, Princeton, N.J.). To measure the spray pattern, the devices were actuated below a sheet of paper that was located 3 cm above the spray nozzle. All measurements were made at ambient room temperature (20-25° C.). The smallest ($D_{min}$) and the largest ($D_{max}$) diameter of the blue pattern formed on the sheet of paper were measured and the results used to calculate the $D_{max}/D_{min}$ ratio, the area of the pattern and the average spray angle. The plume area at 3 cm was calculated using the equation for the area of an ellipse using the half of the two diameters as the ellipse radii. Viscosity of all formulations was measured using Brookfield DV-I viscometer (Brookfield Engineering Laboratories, Inc., Middleboro, Mass.). The results from the measurements are shown in Table 19. Table 19 presents data related to sprayability and viscosity of solvent mixtures used in clonazepam formulations. Viscosity, plume area at 3 cm, spray angle and $D_{max}/D_{min}$ ratio reflecting the symmetry of the spray plume are presented.

TABLE 19

Sprayability and Viscosity

| Composition | Avg. viscosity (cP) | Plume area at 3 cm (cm²) | Spray angle (°) | Ratio $D_{max}/D_{min}$ |
|---|---|---|---|---|
| 80% Glycofurol + 20% Transcutol ® | 11.5 | 5.93 | 49.2 | 1.07 |
| 50% Glycofurol + 50% Transcutol ® | 7.4 | 8.45 | 57.3 | 1.04 |
| 95% Glycofurol + 5% H₂O | 16.7 | 5.73 | 48.6 | 1.22 |
| 70% Glycofurol + 30% Triacetin | 14.6 | 5.78 | 48.7 | 1.12 |
| 60% Transcutol ® + 30% Triacetin + 10% H₂O | 5.8 | 8.71 | 58.1 | 1.03 |
| 60% Transcutol ® + 40% Propylene glycol | 8.8 | 6.42 | 51.0 | 1.11 |
| 70% PEG200 + 30% H₂O | 20.6 | 4.07 | 41.6 | 1.14 |
| 80% PEG200 + 20% H₂O | 30.0 | 4.10 | 43.3 | 2.04 |
| 90% PEG200 + 10% H₂O | 41.7 | 2.46 | 33.6 | 1.79 |
| 80% PEG200 + 10% GF + 10% H₂O | 42.8 | 3.21 | 39.2 | 2.07 |

TABLE 19-continued

Sprayability and Viscosity

| Composition | Avg. viscosity (cP) | Plume area at 3 cm (cm²) | Spray angle (°) | Ratio $D_{max}/D_{min}$ |
|---|---|---|---|---|
| 50% PEG200 + 30% PG + 10% GF + 10% H₂O | 35.4 | 4.55 | 44.9 | 1.54 |
| 60% PG + 30% GF + 10% H₂O | 23.3 | 4.92 | 46.3 | 1.79 |
| 70% PG + 30% GF | 31.7 | 4.32 | 43.1 | 1.22 |
| Water | 1.0 | 15.52 | 73.1 | 1.10 |

While water had a viscosity of 1.0 cP the solvent mixtures tested range from 5.8 (60% Transcutol®+30% Triacetin+10% H₂O) to 42.8 cP (80% PEG200+10% GF+10% H₂O). The viscosity of the solvent mixtures had a negative correlation with plume area and spray angle and plume asymmetry as shown in FIG. 7, FIG. 8 and FIG. 9.

From the data shown in Table 19, FIG. 7, and FIG. 8 it is evident that the spray angle became smaller with increasing viscosity of solvent matrix in the standard Pfeiffer Unit-dose devices. FIG. 9 shows that the plume asymmetry remained within the range 1.0 to 1.2 up to solution viscosity about 20 cP above which irregularity in the plume shape increased. Visual inspection of the appearance of the spray plume of three solutions in the viscosity range from 5.8 to 41.7 revealed that a plume was formed and none of them "squirted."

These results demonstrated that at 20-25° C. all solvent matrices tested spray well from Pfeiffer unit dose devices. The results also suggested that viscosity is a good predictor of sprayability for the formulations of the present invention. As weather may dictate substantially different conditions of use, the effect of temperature on viscosity was determined. A Gilmont falling ball viscometer was filled with diethylene glycol monoethyl ether and calibrated for several hours at each temperature. At −17° C., 8° C., 23° C. and 40° C. the measured viscosity was 6.6 cP, 5.4 cP, 3.8 cP and 3.1 cP, respectively. Hence, with relatively low dependence of temperature on viscosity, the 100% transcutol formulation can be expected to exhibit good spray characteristic over a wide range of temperatures below 40° C. and at least about −15° C. to 3° C.

Example 7

Example Compositions, Formulations, and Method of Making

In one aspect the present invention relates to benzodiazepine compositions formulated for intranasal administration. Unit dosages typically have a volume of between about 25 μL to about 150 μL, preferably about 100 μL. A unit dosage of clonazepam, for example, for the treatment of seizure clusters, is between about 0.1 mg to about 5 mg, preferably about 1 mg to about 4 mg. Table 20 presents example formulations for nasal administration dosage forms. These example formulations provide 10 mg/mL clonazepam.

TABLE 20

Composition of Solution Formulations (% w/w)

| General Component | Specific Component | Formulation I | Formulation II | Formulation III | Formulation IV |
|---|---|---|---|---|---|
| Solvent 1 (high solublization of | diethyleneglycol monoethyl-ether | 49.5 | 49.5 | — | — |

TABLE 20-continued

Composition of Solution Formulations (% w/w)

| General Component | Specific Component | Formulation I | Formulation II | Formulation III | Formulation IV |
|---|---|---|---|---|---|
| clonazepam Solvent 2 (low clonazepam solubility) | glycofurol propylene glycol triacetin | — — 49.5 | — 49.5 — | 49.5 — 49.5 | 49.5 49.5 — |
| Drug | Clonazepam | 1.0 | 1.0 | 1.0 | 1.0 |
| | Total | 100 | 100 | 100 | 100 |

The following methods of making example compositions of the present invention are generally presented and can be modified by one of ordinary skill in the art in view of the teachings of the present specification. Exemplary dosage forms and methods of manufacturing are generally described.

The desired amount of clonazepam was dissolved in solvent 1 at ambient temperature with stirring until the solution is clear and homogeneous. Solvent 2 was then added and the solution was stirred until homogeneous.

Exemplary formulations of the present invention include, but are not limited to, a final concentration of between about 1 w/w % to about 20 w/w % clonazepam, between about 30 w/w % to about 70 w/w % solvent 1, and between about 70 w/w % and about 30 w/w % of solvent 2. Further components may be added as discussed herein above and w/w % composition of the components modified accordingly.

A typical target dose of intranasal clonazepam is 1 to 2 mg per unit dosage. Normally, 1 mg clonazepam (Rivotril i.v.) is administered intravenously by a health care professional in acute epileptic seizure attack. This could be achieved by intranasally administering, for example, 100 μL of a 10 mg/mL solution with 100% bioavailability, a 13.3 mg/mL solution with a 75% bioavailability, or a 20 mg/mL formulation with 50% bioavailability.

Unit or multiple doses may be dispensed into an appropriate delivery device, for example, fixed volume metered dose devices. Devices for intranasal delivery of pharmaceuticals are known in the art (for example, manufactured by Pfeiffer of America, Princeton, N.J. and Valois of America Inc., Greenwich, Conn.). Devices that have the ability to consistently deliver the pharmaceutical composition of the present invention are preferred. Such devices are operable by a patient or second party, for example, medical personnel. Further, these devices leave virtually no residual clonazepam in the device after use. Accordingly, the device can be easily discarded.

Intranasal delivery devices may be modified, for example, by increasing the size of the discharge orifice in the nose piece of the applicator in order to achieve appropriate spray plume and nasal penetration. For example, a discharge orifice of about 0.07 mm may be used to accommodate higher viscosity compositions. The intranasal delivery device components may also be sterilized by methods known in the art. However, as the compositions of the present invention are anhydrous, dry heat, aseptic filtering or terminal sterilization may be necessary. However, if the formulation is microcidal, sterilization or aseptic filling will likely not be needed (see Example 3 above)

Intranasal delivery devices may be filled with single or multi-dose amounts of benzodiazepines. Devices with one or more unit-dose(s) may be sterilized employing methods and technology known in the art. Intranasal delivery devices comprising the benzodiazepine compositions of the present invention may further be sealed with a tamper-proof seal. In addition, appropriate child-proofing control means may also be added to the devices.

The benzodiazepine compositions of the present invention may be packaged under nitrogen in order to reduce oxidative damage to the clonazepam or to the excipients. Similarly, the manufacturing process may also be carried out under limited oxygen conditions.

Example 8

Human Pharmacokinetic Study

The human pharmacokinetics, safety, and tolerability of the benzodiazepines compositions of the present invention formulated for intranasal delivery for therapeutic applications are evaluated using standard clinical procedures. Benzodiazepine compositions formulated for intranasal delivery are provided, for example, for application by the participants to intranasal mucosa.

A primary objective of initial studies in humans is to determine and compare pharmacokinetic profiles of three dosage forms of a benzodiazepine: oral, i.v., and intranasal, following single administration. An example of such a study in humans is a cross-over study performed in 12 healthy male volunteers. Plasma and urine level of clonazepam and 7-amino-clonazepam are determined, for example, using HPLC and UV detection. Secondary objectives of such a study include determination of safety and tolerability of the intranasal clonazepam formulations of the present invention and evaluating their pharmacodynamic effects using qEEG mapping (see, e.g., Example 9, below). Further the initial studies in humans are used to determine local tolerability of intranasal formulation using questionnaire and the Visual Analog Scale (VAS). VAS is a validated instrument that has been used in numerous studies to quantify subjective opening of the nasal passages. In addition, cognitive, sleepiness and mood effects are evaluated using questionnaires and scales (see, e.g., Example 10 below). Further, attention and vigilance may be evaluated using, for example, LEEDS Psychomotor Multiple Choice Reaction Time (MCRT) testing.

Example 9 qEEG Mapping

EEG profiles are determined for patients dosed intranasally with benzodiazepine compositions of the present invention. Vehicle controls without clonazepam may also be administered. Standard frequencies of the EEG bands are as follows: delta (0.5-305 Hz); theta (4-7.5 Hz); alpha (8-12.5 Hz); and beta (13-32 Hz). The latter two are divided into sub-bands as follows: alpha 1 (8-9.5 Hz) and alpha 2 (10-12.5 Hz); and beta 1 (13-17.5 Hz), beta 2 (18-20.5 Hz), and beta 3 (21-32 Hz)

The functional correlates of the EEG bands are as follows: delta, sedative potential; theta, cognition; alpha, vigilance/attention; and beta, arousal/anxiety. Increases in beta bands have been shown to be correlated with subjective anxiolysis (Ansseau, M., et al., "Self-reports of anxiety level and EEG changes after a single dose of benzodiazepines. Double-blind comparison of two forms of oxazepam," Neuropsychobiology 12(4):255-9 (1984).

As a control clonazepam may be administered i.v. at selected doses. Placebo is also administered i.v.

Interkinetic map (absolute energy) of EEG parameters relative to time after administration of clonazepam versus placebo are obtained.

Sedation effects may also be evaluated using, for example, the Stanford sleepiness scale.

These results are expected to support the use of clonazepam compositions formulated for intranasal administration for pharmaceutical applications, for example, for treatment of seizure clusters wherein a rapid onset of anticonvulsive effect is seen with minimal adverse effects (such as minimal increases in sedation).

Example 10

Cognitive Effects of Benzodiazepines

This example describes the pharmacodynamic effects of benzodiazepine compositions formulated for intranasal administration using neurocognitive tests. A selection of tests from a computerized assessment system of Cognitive Drug Research ("CDR," Reading, United Kingdom) is employed. The study is typically a double-blind, randomized, placebo-controlled cross-over design. As a control, the group may receive benzodiazepine intravenous (i.v.) and placebo at selected dosages.

Cognitive function is typically assessed using an attentional task battery to assess attention and a word recognition task to assess secondary memory. Following training on the cognitive test procedures at screening and on Day −1, CDR assessments are typically completed at pre-dose and 30, 60, 90, 120 and 180 minutes post-dose on Day 1 of each period. The attentional task battery and the Word Recognition task from the CDR computerized cognitive assessment system are administered. Parallel forms of the tasks are presented at each assessment to allow for repeated assessment by presenting different, but equivalent stimuli.

Tests may be administered, for example, in the following order: Word Presentation; Simple Reaction Time; Digit Vigilance; Choice Reaction Time; and Word Recognition. Two composite scores were generated from the collected data: Power of Attention, the speed measures from the three attentional tasks all strongly load on a single factor; and Continuity of Attention, the accuracy measures from the attentional tasks Choice Reaction Time and Digit Vigilance both reflect the ability of the subject to sustain attention and avoid error. Summary statistics (m, number; mean; sem, standard error; sd, standard deviation; median; min, minimum; max, maximum; and missing) are typically calculated for each measure at each time point by dose. For each measure, pre-dose (baseline) data is subtracted from the data at each post-dosing time to derive 'difference from baseline' scores. Figures (mean±sem) are plotted using the unadjusted scores and derived 'difference from baseline' scores.

Repeated measures analysis of covariance (ANCOVA) are conducted on the data using, for example, SAS PROC MIXED. Fixed terms are fitted to the model for sequence, dose, period, time and the dose*time interaction. A random effect of subjects within sequence are fitted to the model. Pre-dose (baseline) scores are used as a covariate. Significance is typically tested at the 0.05 level.

For the majority of measures, the selected therapeutic doses of benzodiazepines are expected to show little statistical support for significant impairments. Benzodiazepines are expected to show a pattern of dose dependent impairment of cognition (attention and secondary memory). The size and duration of the impairment will be determined with increasing dose of the benzodiazepine.

Example 11

Solubility of Clonazepam in Glycol Ethers at 25° C.

A number of glycol ether solvents are believed to be acceptable for solubilizing benzodiazepines in intranasal applications. Four glycol ethers were compared, as shown in the table below.

TABLE 21

| | Glycol Ethers | | | |
|---|---|---|---|---|
| # | Name | CAS | Common | Density |
| 1 | 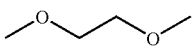<br>1,2-dimethyxoethane | 110-71-4 | monoglyme | 0.867 |
| 2 | 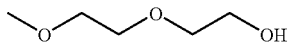<br>Di (ethylene glycol) methyl ether | 111-77-3 | methyl carbitol | 1.023 |
| 3 | 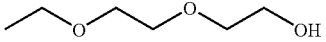<br>Diethylene glycol monoethyl ether | 111-90-0 | Carbitol DEGEE | 0.999 |
| 4 | 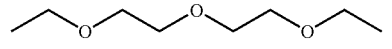<br>Di (ethyleneglycol) diethyl ether | 112-36-7 | Diethyl carbitol | 0.909 |

10 mg of clonazepam was weighed into glass vials used in the Pfeiffer mono-dose spray system (Pfeiffer of America, Princeton, N.J.). Four samples of each of four solvents were prepared as follows. 130-μL of each solvent was pipetted into the vial, which was then stoppered with a black chlorobutyl rubber stopper. The samples were then sonicated for 10 minutes and two of each was stored at 25 C for at least 12 h.

The vials were removed from the chamber, placed inside polyethylene centrifuge vials, and centrifuged for 2 minutes at 5000 rpm. 10 μL of liquid was then sampled from each vial, accurately weighed, and diluted with 1 mL of acetonitrile. The drug concentration was analyzed by UV using an Agilent HPLC system with no column, 10 μL injection volume, acetonitrile mobile phase, 0.3 mL/min and UV detection at 350 nm. The solubilities were calculated from peak area based on calibration with blank and standard solutions, and are shown below.

TABLE 22

Solubilities of Clonazepam in Glycol Ethers

| Solvent | Solubility at 25 C., mg/mL |
|---|---|
| 1,2-dimethyxoethane | 39.3 |
| Di (ethylene glycol) methyl ether | 56.4 |
| Diethylene glycol monoethyl ether (DEGEE) | 41.8 |
| Di (ethyleneglycol) diethyl ether | 19.0 |

Example 12

Solubilities of Clonazepam in Glycol Ethers at 3 Temperatures

Samples were prepared using procedures of Example 11 (25° C. solubilities, included in table below for reference). The samples were stored in the refrigerator or freezer for at least 12 hours, and precipitate had substantially settled. The vials were then centrifuged at −5° C. and 5° C. for the −15° C. and 5° C. samples, respectively, at 5000 rpm for 2 minutes. The solubilities shown below indicate very little temperature dependence on solubility between 25° C. and −15° C. for clonazepam in these glycol ethers. These compositions could be stored at temperatures up to 30° C. and down to −15° C. and retain their stability.

TABLE 23

Solubilities (mg/mL) of Clonazepam in Glycol Ethers

| Solvent | −15 C. | 5 C. | 25 C. |
|---|---|---|---|
| 1,2-dimethyxoethane | 35.2 | 35.7 | 39.3 |
| Di (ethylene glycol) methyl ether | 58.1 | 53.9 | 56.4 |
| Diethylene glycol monoethyl ether | 43.3 | 37.7 | 41.8 |
| Di (ethyleneglycol) diethyl ether | 19.5 | 18.5 | 19.0 |

Example 13

Solubilities of Clonazepam in Water-Containing Solvents

The samples from Example 11, after completing the solubility measurement in 100% solvent, were partly pipetted into another set of glass vials (Pfeiffer mono-dose vials) and mixed with varying proportions of pH6.8 buffered water to form 120 μL aqueous mixtures of 20% to 80% glycol ether. All samples immediately showed precipitation. The vials were stored at 25° C. for approximately 1 day. Prior to sampling, the vials were centrifuged at 5000 rpm for 2 minutes at 23° C. The results are shown below; neat solvent solubilities from Example 11 are included for reference. Increased water content decreases solubility substantially.

TABLE 24

Solubilities (mg/mL) of Clonazepam in Solvent/Water Solutions

| | % Solvent | | | | |
|---|---|---|---|---|---|
| Solvent | 100 | 80 | 60 | 40 | 20 |
| % Water | 0 | 20 | 40 | 60 | 80 |
| 1,2-dimethyxoethane | 39.3 | 29.6 | 9.2 | 0.64 | 0.18 |
| Di (ethylene glycol) methyl ether | 56.4 | 18.9 | 2.8 | 1.00 | 0.26 |
| Diethylene glycol monoethyl ether | 41.8 | 21.8 | 4.5 | 0.52 | 0.30 |
| Di (ethyleneglycol) diethyl ether | 19.0 | 38.8 | 8.5 | 1.23 | 0.31 |

Example 14

Human Pharmacokinetic Study Results

A human pharmacokinetic study was carried out as described in Example 8.

15 young, healthy male volunteers received a single dose of 1 mg clonazepam by oral, intravenous and intranasal routes in a three-period cross-over design. The intranasal formulation of clonazepam produced its median $T_{max}$ at 0.200 hours (approximately 12 minutes) post-dose while the median $T_{max}$ was 2 hours after oral administration and the median $T_{max}$ following intraveneous administration was 0.10 hours. The mean $C_{max}$ values after administration of 1 mg of clonazepam by the oral, intranasal routes were comparable (intranasal route: mean±SD, 7.12±3.81 ng/mL and oral route: mean±SD, 7.64±1.74 ng/mL; and intravenous route: mean±SD, 42.5±10.8). Accordingly, $C_{max}$ of the intranasal route was 93% of that of the oral route and 17% of that of the intravenous route.

AUCs at 24 hours after administration of 1 mg of clonazepam were similar for the intravenous and oral routes (approximately 106 and 95 ng·h/mL, respectively), while the AUC at 24 hours after intranasal administration (approximately 58 ng·h/mL) was roughly half that observed after intravenous administration. Accordingly $AUC_{in}:AUC_{iv}=1:1.83$ and $AUC_{in}:AUC_{oral}=1:1.64$ and the bioavailability was 55% relative to intravenous and 61% relative to oral.

Somnolence and nasal discomfort were the most common side effects reported in the study (75.6% and 26.7%, respectively). Somnolence was reported by 10 of 15 (approximately 67%) subjects after intranasal dosing and 13 of 15 (approximately 87%) subjects after oral dosing. Approximately 93% of the subjects reported somnolence or sedation (11/15 for somnolence and 3/15 for sedation) after intravenous dosing. Nasal discomfort was reported by 12 of 15 subjects (approximately 80%) after intranasal dosing. There were no clinically relevant changes in laboratory parameters, After administration of 1 mg of clonazepam, 7-Aminoclonazepam concentrations increased continuously over the 24-hour blood sample collection period for all three routes of administration. The mean $C_{max}$ for the intranasal route (1.17 ng/mL) was lower than values observed for the intravenous and oral routes. The mean $C_{max}$ was similar for the intravenous and oral routes (approximately 2 ng/mL). The mean $AUC_t$ for the intranasal route (16.9 ng·h/mL) was lower than values observed for the intravenous and oral routes. The mean $AUC_t$ was similar for the intravenous and oral routes (approximately 30 ng·h/mL).

Example 15 qEEG Mapping Results

EEG profiles were determined as described in Example 9 for the 15 volunteers described in Example 14. Based on changes from baseline, clonazepam produced EEG changes characteristic of benzodiazepines. Effects were greatest after intravenous administration, followed by intranasal and oral routes of administration. Statistically significant differences between routes of administration occurred at different time points, indirectly demonstrating different time courses for different effects. In general, clonazepam administration by all three routes increased delta and beta activity and decreased alpha and theta activity on the EEG. This pattern of activity was noted soon after administration of clonazepam by the intranasal and intravenous routes (i.e., within the first 3 to 6 minutes after dosing) and occurred later after oral administration (at approximately 2 hours after dosing).

A post-hoc analysis focusing on the time course of effects for beta-1 relative power established that intranasal administration of clonazepam is efficient, with a magnitude of effect similar to that from oral administration and an intermediate time delay of action between the intravenous and oral routes. Together with the EEG profile in the delta, theta, and alpha bands from mapping analysis, these results are in agreement with previous pharmacodynamic changes reported with various benzodiazepine drugs.

Example 16

Cognitive Effects of Clonazepam

Psychomotor and subjective test results were obtained as described in Example 10 for the 15 volunteers described in Example 14. Intranasal clonazepam spray was shown to possess a rapid onset of action comparable to the intravenous formulation on objective tests (Leeds Psychomotor Test) and subjective tests (Bond and Lader VAS and Karolinska Sleepiness Scale). Effects with intravenous and intranasal administration were first apparent at approximately 30 minutes while effects with oral administration were first apparent at approximately 2 hours.

We claim:

1. A pharmaceutical composition for transmucosal administration to a mammal, comprising
a solvent system consisting essentially of a first solvent in which benzodiazepine is soluble, wherein the first solvent is composed of one or more components selected from the group consisting of diethyleneglycol monoethylether and tetrahydrofurfuryl alcohol polyethyleneglycol ether, the first solvent capable of penetrating nasal mucosal tissue, and a second solvent in which benzodiazepine is less soluble than in the first solvent, wherein the second solvent is composed of one or more components selected from the group consisting of glycerol triacetate and propylene glycol, and 10% (weight/weight) or less of an aqueous buffer solution, with the caveat that the solvent system does not comprise free polyethylene glycol polymers; and
a therapeutically effective amount of a benzodiazepine;
the composition being a single phase and homogeneous liquid composition; and,
wherein the composition is formulated to have a viscosity of less than about 32 cP at temperatures between 20-25° C.

2. The composition of claim 1, wherein the solvent system is free of aqueous buffer.

3. The composition of claim 1, wherein the first solvent is present at a weight percent of between about 30% to about 70%.

4. The composition of claim 1, wherein the benzodiazepine is selected from the group consisting of alprazolam, bromazepam, chlordiazepoxide, clobazam, clonazepam, clorazepate, diazepam, estazolam, flunitrazepam, flurazepam, halazepam, ketazolam, loprazolam, lorazepam, lormetazepam, medazepam, midazolam, nitrazepam, nordazepam, oxazepam, prazepam, quazepam, temazepam, tetrazepam, and triazolam.

5. The composition of claim 4, wherein the benzodiazepine is selected from the group consisting of lorazepam and diazepam.

6. The composition of claim 1, wherein the first and second solvents are present in equal weight percents.

7. The composition of claim 1, wherein the pH of the aqueous buffer solution is between about pH 2 to about pH 7.

8. The composition of claim 1, further comprising one or more non-solvent components selected from the group consisting of surfactant, anti-oxidant, lipid, mucosa penetration enhancing agent, colorant, flavoring agent, anesthetic agent, and agent to adjust osmolarity.

9. The composition of claim 1, wherein the solvent system is a binary solvent system.

10. The composition of claim 9, wherein the binary solvent system is free of the aqueous buffer.

11. The composition of claim 1, further comprising less than about 10% (weight/weight) of one or more non-solvent components selected from the group consisting of surfactant, anti-oxidant, lipid, mucosa penetration enhancing agent, colorant, flavoring agent, anesthetic agent, and agent to adjust osmolarity.

12. The composition of claim 11, wherein one component comprises a mucosal penetration enhancing agent.

13. The composition of claim 12 wherein the penetration enhancing agent is selected from the group consisting of selected from N-methyl-2-pyrrolidone, 2-pyrrolidone, propylene glycol, dimethylformamide, dimethyl sulfoxide, caprolactam, oleic acid, decylmethylsulfoxide, 1-dodecylazacycloheptan-2-one, isopropyl myristate, hexamethylene palmitamide, hexamethylene lauramide, aliphatic acids, esters, and combinations thereof.

14. The composition of claim 11, wherein one component comprises an antioxidant.

15. The composition of claim 14, wherein the antioxidant is selected from the group consisting of edetic acid, butylhydroxytoluene, propyl gallate, sodium metabisulfite, butylhydroxyanisole, tocopherols and combinations thereof.

16. The composition of claim 11, wherein one component comprises a colorant.

17. The composition of claim 11, wherein one component comprises a flavorant.

18. The composition of claim 11, wherein one component comprises an anesthetic agent.

19. The composition of claim 1, wherein the composition is used at a unit therapeutic dose of between 50 μL and 300 μL.

20. The composition of claim 19, wherein the composition is used at a unit therapeutic dose of between 25 μL and 150 μL.

21. The composition of claim 5, wherein the therapeutically effective amount of diazepam is between 2.0 mg and 40 mg per unit dose.

22. The composition of claim 5, wherein the therapeutically effective amount of lorazepam is between 0.5 mg and 10.0 mg per unit dose.

23. The composition of claim 1, wherein the mammal is a human.

24. The pharmaceutical composition of claim 1 comprising a benzodiazepine for transmucosal administration to a mammal, characterized by (i) a $T_{max}$ of the benzodiazepine, after a single transmucosal administration, of no more than 2 hours and (ii) a bioavailability of the benzodiazepine, after a single transmucosal administration, of no less than 30% of the bioavailability of an equivalent dose of the benzodiazepine delivered orally.

25. The composition of claim 24 wherein the $T_{max}$ of the benzodiazepine, after a single transmucosal administration, is less than or equal to 30 minutes and the bioavailability of the benzodiazepine, after a single transmucosal administration, is greater than or equal to 55% of the bioavailability of an equivalent dose of the benzodiazepine delivered orally.

26. The composition of claim 24 wherein the transmucosal delivery is via the intranasal route.

27. The pharmaceutical composition of claim 1 comprising a benzodiazepine for transmucosal administration to a mammal, characterized by (i) a $C_{max}$ of the benzodiazepine, after a single transmucosal administration, of at least about 75% of the $C_{max}$ of an equivalent dose of the benzodiazepine delivered orally, and (ii) a bioavailability of the benzodiazepine, after a single transmucosal administration, of no less than 30% of the bioavailability of an equivalent dose of benzodiazepine delivered orally.

28. The composition of claim 27 wherein the $C_{max}$ of a benzodiazepine, after a single transmucosal administration, greater than or equal to 90% of the $C_{max}$ of an equivalent dose of the benzodiazepine delivered orally, and a bioavailability of the benzodiazepine, after a single transmucosal administration, is greater than or equal to 55% of the bioavailability of an equivalent dose of the benzodiazepine delivered orally.

29. The composition of claim 27 wherein the transmucosal delivery is via the intranasal route.

30. The pharmaceutical composition of claim 1 comprising a benzodiazepine for intranasal administration to a mammal, characterized by (i) a ratio of the AUC of the benzodiazepine, after a single intranasal administration, ($AUC_{in}$) to the AUC of an equivalent dose of the benzodiazepine delivered orally ($AUC_{oral}$) of at least about $AUC_{in}:AUC_{oral}=1:1.33$, wherein the AUC values are determined over the same time period.

31. The pharmaceutical composition of claim 1, wherein the aqueous buffer solution comprises a phosphate buffer, a carbonate buffer, a citrate buffer, an acetate buffer, sodium hydroxide, hydrochloric acid, lactic acid, tartaric acid, diethylamine, triethylamine, diisopropylamine, or aminomethylamine, or any combination thereof.

32. The pharmaceutical composition of claim 1 further comprising sodium edetate or edetic acid, or a combination thereof.

* * * * *

UNITED STATES PATENT AND TRADEMARK OFFICE
CERTIFICATE OF CORRECTION

PATENT NO.         : 8,609,651 B2
APPLICATION NO.    : 11/897028
DATED              : December 17, 2013
INVENTOR(S)        : Jamieson et al.

Page 1 of 5

It is certified that error appears in the above-identified patent and that said Letters Patent is hereby corrected as shown below:

On the Title page, in column 2, under "Other Publications", line 1, delete "07811570.6 ," and insert --07811570.6,--, therefor On the Title page, in column 2, under "Other Publications", line 2, delete "Filed" and insert --filed--, therefor On the Title page, in column 2, under "Other Publications", line 2, delete "pgs" and insert --pgs.--, therefor On the Title page, in column 2, under "Other Publications", line 4, delete "Filed" and insert --filed--, therefor On the Title page, in column 2, under "Other Publications", line 12, delete "9 pgs. ." and insert --9 pgs.--, therefor On Title page 2, in column 1, under "Other Publications", line 1, before "Response", delete "Office Action", therefor On Title page 2, in column 1, under "Other Publications", line 30, delete "197275,Office" and insert --197275, Office--, therefor On Title page 2, in column 1, under "Other Publications", line 33, delete "Filed" and insert --filed--, therefor On Title page 2, in column 1, under "Other Publications", line 36, delete "07811570.6 ," and insert --07811570.6,--, therefor On Title page 2, in column 1, under "Other Publications", line 40, delete "Mailed" and insert --mailed--, therefor Signed and Sealed this
Sixth Day of May, 2014

Michelle K. Lee
*Deputy Director of the United States Patent and Trademark Office*

CERTIFICATE OF CORRECTION (continued)
U.S. Pat. No. 8,609,651 B2

On Title page 2, in column 1, under "Other Publications", line 45, delete "P," and insert --P.,-- therefor On Title page 2, in column 1, under "Other Publications", line 62, delete "K," and insert --K.,-- therefor On Title page 2, in column 1, under "Other Publications", line 65, delete "11/897,002 ," and insert --11/897,002,-- therefor On Title page 2, in column 2, under "Other Publications", line 17, delete "11/897,002 ," and insert --11/897,002,-- therefor On Title page 2, in column 2, under "Other Publications", line 27, before "Response", delete "Office Action", therefor On Title page 2, in column 2, under "Other Publications", line 43, delete "11/897,002 ," and insert --11/897,002,-- therefor On Title page 2, in column 2, under "Other Publications", line 61, delete "P," and insert --P.,-- therefor In the Specification In column 2, line 13, delete "appears," and insert --appears-- therefor In column 2, line 56, delete "phenyloin" and insert --phenytoin-- therefor In column 5, line 29, delete "phobia;" and insert --phobia,-- therefor In column 5, line 64, delete "CLZ20T80P02T, 10" and insert --CLZ20T80P02T-10-- therefor In column 9, line 59, delete "intraveneously" and insert --intravenously-- therefor In column 10, line 27, delete "poly ethylene" and insert --polyethylene-- therefor In column 12, line 26, delete "solublizing" and insert --solubilizing-- therefor In column 13, line 10, delete "also," and insert --also-- therefor In column 14, line 7, delete "solublization" and insert --solubilization-- therefor In column 16, line 27, delete "glycerol," and insert --glycerol-- therefor In column 16, line 32, delete "ether" and insert --ether.-- therefor In column 17, line 9, delete "solublizing" and insert --solubilizing--, therefor In column 18, line 58, delete "$AUC_{in}$ $AUC_{oral}$" and insert --$AUC_{in}$:$AUC_{oral}$--, therefor In column 19, line 51, delete "Benzodiazepine Compositions" and insert --benzodiazepine compositions--, therefor In column 19, line 52, delete "Present Invention" and insert --present invention--, therefor In column 21, line 53-54, delete "solublizing" and insert --solubilizing--, therefor In column 21, line 60, delete "solublizing" and insert --solubilizing--, therefor In column 23, line 59, delete "solublizers," and insert --solubilizers,--, therefor In column 24, line 2, delete "0.200" and insert --200--, therefor In column 25, line 63, delete "M" and insert --M.--, therefor In column 26, line 48, delete "U," and insert --U.,--, therefor In column 26, line 50, delete "F," and insert --F.,--, therefor In column 26, line 53, delete "A W," and insert --A. W.,--, therefor In column 26, line 56, delete "M P," and insert --M. P.,--, therefor In column 27, line 19, delete "K T," and insert --K. T.,--, therefor In column 33, Table 10, Entry 12, delete "Transcutol" and insert --Transcutol ®--, therefor In column 35, line 5, delete "CLZ20T80P02T, 10" and insert --CLZ20T80P02T-10--, therefor In column 35, line 27, delete "signal:" and insert --signal.--, therefor In column 35, line 39, delete "H2O" and insert --$H_2O$--, therefor In column 38, line 9, delete "Transcutol®V" and insert --Transcutol®--, therefor In column 38, line 17, delete "F %" and insert --F%--, therefor In column 43, line 3, delete "solublization" and insert --solubilization--, therefor In column 43, line 8, delete "first-solvent" and insert --first solvent--, therefor

CERTIFICATE OF CORRECTION (continued)
U.S. Pat. No. 8,609,651 B2

In column 44, line 40, delete "Sek" and insert --Sex--, therefor

In column 48, line 42 (Approx.), delete "3° C." and insert --30° C.--, therefor

In column 48, Table 20, Line 6, delete "solublization" and insert --solubilization--, therefor In column 51, line 2, after "Hz)", insert --.--, therefor In column 52, line 14, delete "(m," and insert --(n,--, therefor In column 53, line 7, delete "25 C" and insert --25° C.--, therefor In column 53, line 23, (Approx.) Table 22, delete "25 C." and insert --25° C.--, therefor In column 53, line 24, (Approx.) Table 22, delete "dimethyxoethane" and insert --dimethoxyethane--, therefor In column 53, line 26, (Approx.) Table 22, delete "Diethylene glycol" and insert --Di (ethylene glycol)--, therefor In column 53, line 28, (Approx.) Table 22, delete "(ethyleneglycol)" and insert --(ethylene glycol)--, therefor In column 53, line 50, (Approx.) Table 23, delete "-15 C." and insert -- -15° C.--, therefor In column 53, line 50, (Approx.) Table 23, delete "5 C." and insert --5° C.--, therefor In column 53, line 50, (Approx.) Table 23, delete "25 C." and insert --25° C.--, therefor In column 53, line 52, (Approx.) Table 23, delete "dimethyxoethane" and insert --dimethoxyethane--, therefor In column 53, line 55-56, (Approx.) Table 23, delete "Diethylene glycol" and insert --Di (ethylene glycol)--, therefor In column 53, line 58, (Approx.) Table 23, delete "(ethyleneglycol)" and insert --(ethylene glycol)--, therefor In column 54, line 19, (Approx.) Table 24, delete "dimethyxoethane" and insert --dimethoxyethane--, therefor In column 54, line 22, (Approx.) Table 24, delete "Diethylene glycol" and insert --Di (ethylene glycol)--, therefor In column 54, line 24, (Approx.) Table 24, delete "(ethyleneglycol)" and insert --(ethylene glycol)--, therefor In column 54, line 40, delete "intraveneous" and insert --intravenous--, therefor In the Claims In column 55, line 56, in Claim 1, after "comprising", insert --:--, therefor In column 56, line 6, in Claim 1, delete "and," and insert --and--, therefor In column 58, line 19, in Claim 30, delete "($AUC_{min}$)" and insert --($AUC_{in}$)--, therefor